US007423014B2

(12) United States Patent
Ekwuribe et al.

(10) Patent No.: US 7,423,014 B2
(45) Date of Patent: *Sep. 9, 2008

(54) INSULIN CONJUGATES FOR TREATING DIABETES MELLITUS

(75) Inventors: Nnochiri N. Ekwuribe, Cary, NC (US); Christopher H. Price, Chapel Hill, NC (US); James Gordon Still, Raleigh, NC (US); Jennifer Ann Filbey, Raleigh, NC (US); Aslam M. Ansari, Montgomery Village, MD (US); Amy L. Odenbaugh, Morrisville, NC (US); Balasingam Radhakrishnan, Chapel Hill, NC (US)

(73) Assignee: Biocon Limited (IN)

( * ) Notice: Subject to any disclaimer, the term of this patent is extended or adjusted under 35 U.S.C. 154(b) by 0 days.

This patent is subject to a terminal disclaimer.

(21) Appl. No.: 11/314,309

(22) Filed: Dec. 21, 2005

(65) Prior Publication Data

US 2006/0100137 A1    May 11, 2006

Related U.S. Application Data

(63) Continuation of application No. 10/075,097, filed on Feb. 13, 2002, now Pat. No. 7,060,675.

(60) Provisional application No. 60/347,713, filed on Jan. 11, 2002, provisional application No. 60/269,198, filed on Feb. 15, 2001.

(51) Int. Cl.
*A61K 38/28* (2006.01)
*A61K 47/48* (2006.01)

(52) U.S. Cl. .......................................... 514/3

(58) Field of Classification Search ........................ None
See application file for complete search history.

(56) References Cited

U.S. PATENT DOCUMENTS

| | | | |
|---|---|---|---|
| 3,256,153 A | 6/1966 | Heimlech |
| 3,852,353 A | 12/1974 | Heaphy |
| 3,868,356 A | 2/1975 | Smyth |
| 3,919,411 A | 11/1975 | Glass et al. |
| 3,950,517 A | 4/1976 | Lindsay et al. |
| 4,003,792 A | 1/1977 | Mill et al. |
| 4,044,196 A | 8/1977 | Huper et al. |
| 4,087,390 A | 5/1978 | Shields |
| 4,093,574 A | 6/1978 | Shields |
| 4,100,117 A | 7/1978 | Shields |
| 4,179,337 A | 12/1979 | Davis et al. |
| 4,229,438 A | 10/1980 | Fujino et al. |
| 4,253,998 A | 3/1981 | Sarantakis |
| 4,277,394 A | 7/1981 | Fujino et al. |
| 4,338,306 A | 7/1982 | Kitao et al. |
| 4,348,387 A | 9/1982 | Brownlee et al. |
| 4,410,547 A | 10/1983 | Ueno et al. |
| 4,469,681 A | 9/1984 | Brownlee et al. |
| 4,472,382 A | 9/1984 | Labrie et al. |
| 4,526,938 A | 7/1985 | Churchill et al. |
| 4,554,101 A | 11/1985 | Hopp |
| 4,579,730 A | 4/1986 | Kidron et al. |
| 4,582,820 A | 4/1986 | Teng |
| 4,585,754 A | 4/1986 | Meisner et al. |
| 4,602,043 A | 7/1986 | Geho |
| 4,622,392 A | 11/1986 | Hong et al. |
| 4,662,872 A | 5/1987 | Cané |
| 4,684,524 A | 8/1987 | Eckenhoff et al. |
| 4,698,264 A | 10/1987 | Steinke |
| 4,704,394 A | 11/1987 | Geho |
| 4,717,566 A | 1/1988 | Eckenhoff et al. |
| 4,744,976 A | 5/1988 | Snipes et al. |
| 4,761,287 A | 8/1988 | Geho |
| 4,772,471 A | 9/1988 | Vanlerberghe et al. |
| 4,797,288 A | 1/1989 | Sharma et al. |
| 4,822,337 A | 4/1989 | Newhouse et al. |
| 4,839,341 A | 6/1989 | Massey et al. |
| 4,840,799 A | 6/1989 | Applegren et al. |
| 4,849,227 A | 7/1989 | Cho |
| 4,849,405 A | 7/1989 | Ecanow |
| 4,863,896 A | 9/1989 | Geho et al. |
| 4,898,733 A | 2/1990 | DePrince et al. |
| 4,917,888 A | 4/1990 | Katre et al. |

(Continued)

FOREIGN PATENT DOCUMENTS

EP    0 354 855 B1    2/1990

(Continued)

OTHER PUBLICATIONS

B. Radha Krishnan, et al. Proceed. Int'l. Symp. Control. Rel. Bioact. Mater. (2000) 27, pp. 1038-1039.*

(Continued)

*Primary Examiner*—Andrew D Kosar
(74) *Attorney, Agent, or Firm*—Marianne Fuierer; Moore & Van Allen PLLC

(57) ABSTRACT

Methods of treating diabetes mellitus in a patient in need of such treatment include administering an effective amount of an insulin polypeptide-oligomer conjugate of formula V

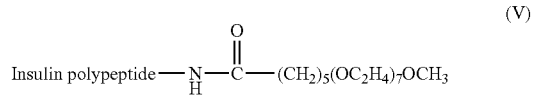

to the patient in order to treat diabetes mellitus in the patient. Methods according to the present invention may "activate" the liver, potentially restoring normal glucose homeostasis to individuals suffering from diabetes mellitus.

8 Claims, 19 Drawing Sheets

U.S. PATENT DOCUMENTS

| | | |
|---|---|---|
| 4,935,246 A | 6/1990 | Ahrens |
| 4,946,828 A | 8/1990 | Markussen |
| 4,957,910 A | 9/1990 | Sutton et al. |
| 4,963,367 A | 10/1990 | Ecanow |
| 4,963,526 A | 10/1990 | Ecanow |
| 4,994,439 A | 2/1991 | Longenecker et al. |
| 5,008,241 A * | 4/1991 | Markussen et al. ............ 514/3 |
| 5,013,556 A | 5/1991 | Woodle et al. |
| 5,055,300 A | 10/1991 | Gupta |
| 5,055,304 A | 10/1991 | Makino et al. |
| 5,089,261 A | 2/1992 | Nitecki et al. |
| 5,093,198 A | 3/1992 | Speaker et al. |
| 5,108,568 A | 4/1992 | Van Alstine |
| 5,157,021 A | 10/1992 | Balschmidt et al. |
| 5,162,430 A | 11/1992 | Rhee et al. |
| 5,164,366 A | 11/1992 | Balschmidt et al. |
| 5,202,415 A | 4/1993 | Jonassen et al. |
| 5,206,219 A | 4/1993 | Desai |
| 5,283,236 A | 2/1994 | Chiou |
| 5,286,637 A | 2/1994 | Veronese et al. |
| 5,292,802 A | 3/1994 | Rhee et al. |
| 5,304,473 A | 4/1994 | Belagaje et al. |
| 5,308,889 A | 5/1994 | Rhee et al. |
| 5,312,808 A | 5/1994 | Shorr et al. |
| 5,320,094 A | 6/1994 | Laube et al. |
| 5,321,009 A | 6/1994 | Baeder et al. |
| 5,324,775 A | 6/1994 | Rhee et al. |
| 5,328,955 A | 7/1994 | Rhee et al. |
| 5,359,030 A | 10/1994 | Ekwuribe |
| 5,364,838 A | 11/1994 | Rubsamen |
| 5,405,621 A | 4/1995 | Sipos |
| 5,405,877 A | 4/1995 | Greenwald et al. |
| 5,413,791 A | 5/1995 | Rhee et al. |
| 5,415,872 A | 5/1995 | Sipos |
| 5,420,108 A | 5/1995 | Shohet |
| 5,438,040 A | 8/1995 | Ekwuribe |
| 5,444,041 A | 8/1995 | Owen et al. |
| 5,446,091 A | 8/1995 | Rhee et al. |
| 5,457,066 A | 10/1995 | Frank et al. |
| 5,461,031 A | 10/1995 | De Felippis |
| 5,468,478 A | 11/1995 | Saifer et al. |
| 5,468,727 A | 11/1995 | Phillips et al. |
| 5,504,188 A | 4/1996 | Baker et al. |
| 5,506,203 A | 4/1996 | Backstrom et al. |
| 5,518,998 A | 5/1996 | Backstrom et al. |
| 5,523,348 A | 6/1996 | Rhee et al. |
| 5,529,915 A | 6/1996 | Phillips et al. |
| 5,545,618 A | 8/1996 | Buckley et al. |
| 5,550,188 A | 8/1996 | Rhee et al. |
| 5,567,422 A | 10/1996 | Greenwald |
| 5,597,797 A | 1/1997 | Clark et al. |
| 5,606,038 A | 2/1997 | Regen |
| 5,612,460 A | 3/1997 | Zalipsky |
| 5,631,347 A | 5/1997 | Baker et al. |
| 5,637,749 A | 6/1997 | Greenwald |
| 5,646,242 A | 7/1997 | Baker et al. |
| 5,650,388 A | 7/1997 | Shorr et al. |
| 5,653,987 A | 8/1997 | Modi et al. |
| 5,658,878 A | 8/1997 | Backstrom et al. |
| 5,681,567 A | 10/1997 | Martinez et al. |
| 5,681,811 A | 10/1997 | Ekwuribe |
| 5,693,609 A | 12/1997 | Baker et al. |
| 5,693,769 A | 12/1997 | Kahne et al. |
| 5,700,662 A * | 12/1997 | Chance et al. ............ 435/69.4 |
| 5,700,904 A | 12/1997 | Baker et al. |
| 5,704,910 A | 1/1998 | Humes |
| 5,707,648 A | 1/1998 | Yiv |
| 5,714,519 A | 2/1998 | Cincotta et al. |
| 5,716,927 A * | 2/1998 | Balschmidt et al. ............ 514/3 |
| 5,738,846 A | 4/1998 | Greenwald et al. |
| 5,747,445 A | 5/1998 | Backstrom et al. |
| 5,747,642 A | 5/1998 | De Felippis |
| 5,750,497 A | 5/1998 | Havelund et al. |
| 5,763,396 A | 6/1998 | Weiner et al. |
| 5,766,620 A | 6/1998 | Heiber et al. |
| 5,824,638 A | 10/1998 | Burnside et al. |
| 5,830,853 A | 11/1998 | Backstrom et al. |
| 5,830,918 A | 11/1998 | Sportsman et al. |
| 5,843,886 A | 12/1998 | Weiner et al. |
| 5,843,887 A | 12/1998 | Petit et al. |
| 5,849,860 A | 12/1998 | Hakimi et al. |
| 5,853,748 A | 12/1998 | New |
| 5,854,208 A | 12/1998 | Jones et al. |
| 5,856,451 A | 1/1999 | Olsen et al. |
| 5,866,538 A | 2/1999 | Norup et al. |
| 5,866,584 A | 2/1999 | Cincotta et al. |
| 5,874,111 A | 2/1999 | Maitra et al. |
| 5,898,028 A | 4/1999 | Jensen et al. |
| 5,902,588 A | 5/1999 | Greenwald et al. |
| 5,905,140 A | 5/1999 | Hansen |
| 5,907,030 A | 5/1999 | Shen et al. |
| 5,922,675 A | 7/1999 | Baker et al. |
| 5,932,462 A | 8/1999 | Harris et al. |
| 5,942,248 A | 8/1999 | Barnwell |
| 5,948,751 A | 9/1999 | Kimer et al. |
| 5,952,008 A | 9/1999 | Backstrom et al. |
| 5,952,297 A | 9/1999 | De Felippis et al. |
| 5,962,267 A | 10/1999 | Shin et al. |
| 5,968,549 A | 10/1999 | New et al. |
| 5,969,040 A | 10/1999 | Hallahan et al. |
| 5,981,709 A | 11/1999 | Greenwald et al. |
| 5,985,263 A | 11/1999 | Lee et al. |
| 5,997,848 A | 12/1999 | Patton et al. |
| 6,004,574 A | 12/1999 | Backstrom et al. |
| 6,025,325 A | 2/2000 | Campfield et al. |
| 6,034,054 A | 3/2000 | De Felippis et al. |
| 6,042,822 A | 3/2000 | Gilbert et al. |
| 6,043,214 A | 3/2000 | Jensen et al. |
| 6,051,551 A | 4/2000 | Hughes et al. |
| 6,057,292 A | 5/2000 | Cunningham et al. |
| 6,063,761 A | 5/2000 | Jones et al. |
| 6,093,391 A | 7/2000 | Kabanov et al. |
| 6,113,906 A | 9/2000 | Greenwald et al. |
| 6,147,108 A | 11/2000 | Hauptman |
| 6,165,976 A | 12/2000 | Backstrom et al. |
| 6,177,087 B1 | 1/2001 | Greenwald et al. |
| 6,191,105 B1 * | 2/2001 | Ekwuribe et al. ............ 514/3 |
| 6,200,602 B1 | 3/2001 | Watts et al. |
| 6,211,144 B1 | 4/2001 | Havelund |
| 6,248,363 B1 | 6/2001 | Patel et al. |
| 6,251,856 B1 | 6/2001 | Markussen et al. |
| 6,258,377 B1 | 7/2001 | New et al. |
| 6,268,335 B1 | 7/2001 | Brader |
| 6,306,440 B1 | 10/2001 | Backstrom et al. |
| 6,309,633 B1 | 10/2001 | Ekwuribe et al. |
| 6,310,038 B1 | 10/2001 | Havelund |
| 6,323,311 B1 | 11/2001 | Liu et al. |
| 6,335,316 B1 | 1/2002 | Hughes et al. |
| 6,342,225 B1 | 1/2002 | Jones et al. |
| 6,506,730 B1 | 1/2003 | Lee et al. |
| 6,828,297 B2 * | 12/2004 | Ekwuribe et al. ............ 514/3 |
| 6,867,183 B2 * | 3/2005 | Soltero et al. ............ 514/3 |
| 6,913,903 B2 * | 7/2005 | Soltero et al. ............ 435/68.1 |
| 7,060,675 B2 * | 6/2006 | Ekwuribe et al. ............ 514/3 |
| 7,084,114 B2 * | 8/2006 | Ekwuribe et al. ............ 514/3 |
| 2002/0160938 A1 | 10/2002 | Brandenburg et al. |
| 2003/0004304 A1 | 1/2003 | Ekwuribe et al. |
| 2003/0027995 A1 | 2/2003 | Ekwuribe et al. |
| 2003/0050228 A1 | 3/2003 | Ekwuribe et al. |
| 2003/0060606 A1 | 3/2003 | Ekwuribe et al. |
| 2003/0069170 A1 | 4/2003 | Soltero et al. |
| 2003/0083232 A1 | 5/2003 | Soltero et al. |
| 2003/0087808 A1 | 5/2003 | Soltero et al. |
| 2003/0144468 A1 | 7/2003 | Ekwuribe et al. |

| | | | |
|---|---|---|---|
| 2005/0080001 A1* | 4/2005 | Soltero et al. | 514/3 |
| 2005/0277580 A1* | 12/2005 | Radhakrishnan et al. | 514/3 |
| 2006/0018874 A1* | 1/2006 | Radhakrishnan et al. | 424/85.4 |
| 2006/0019873 A1* | 1/2006 | Radhakrishnan et al. | 514/3 |
| 2006/0019874 A1* | 1/2006 | Radhakrishnan et al. | 514/3 |
| 2006/0199759 A1* | 9/2006 | Ekwuribe et al. | 514/3 |

FOREIGN PATENT DOCUMENTS

| | | |
|---|---|---|
| EP | 0 381 070 A1 | 8/1990 |
| EP | 0 092 918 B1 | 10/1998 |
| WO | WO 8910937 A1 * | 11/1989 |
| WO | WO 00/43034 | 7/2000 |
| WO | 00/78302 | 12/2000 |
| WO | WO 00/78302 | 12/2000 |
| WO | WO 02/098232 | 12/2002 |
| WO | WO 02/098446 | 12/2002 |
| WO | WO 03/022208 | 3/2003 |
| WO | WO 03/022210 | 3/2003 |
| WO | WO 03/022996 | 3/2003 |

OTHER PUBLICATIONS

B. Radha Krishnan, et al. Proceed. Int'l. Symp. Control. Rel. Bioact. Mater. (1998) 25, pp. 124-125.*

B. Radha Krishnan, et al. Program and Abstracts, 1999 National Meeting of the Ameri. Assoc. Pharm. Scient., New Orleans, LA (1999) Abstract.*

Z. Vajo and W.C. Duckworth. Pharm. Rev. (2000) 52(1), pp. 1-9.*

J. P. Richards, et al. Pharm. Res. (1998) 15(9), pp. 1434-1441.*

Y.P. Shvachkin, et al. Bioorgnicheskaya Khimiya. (1984) 10(5), pp. 708-709.*

Muneaki Hashimoto et al.; Synthesis of Palmitoyl Derivatives of Insulin and Their Biological Activities; Pharmaceutical Research; 1989; vol. 6, No. 2, pp. 171-176; Plenum Publishing Corporation.

Samuel Zlipsky; Synthesis of an End-Group Functionalized Polyethylene Glycol-Lipid Conjugate for Preparation of Polymer-Grafted Liposomes; Bioconjugate Chemistry; 1993; 4, No. 4, pp. 296-299; American Chemical Society.

Vajo, Z et al. Pharm. Rev. (2000) 52, pp. 1-9.

Rudinger, I, In Peptide Hormones, JA Parson, ED. (1976) 1-7.

* cited by examiner

INSULIN CONJUGATES FOR TREATING DIABETES MELLITUS

RELATED APPLICATIONS

This application is a continuation of U.S. patent application Ser. No. 10/075,097, filed Feb. 13, 2002, entitled "METHODS OF TREATING DIABETES MELLITUS", now U.S. Pat. No. 7,060,675, issued Jun. 13, 2006, which claims priority to U.S. Provisional Application No. 60/269,198, filed Feb. 15, 2001, and U.S. Provisional Application No. 60/347,713, filed Jan. 11, 2002, the disclosures of which are incorporated herein by reference in their entireties.

FIELD OF THE INVENTION

The present invention relates to methods of treating diabetes mellitus.

BACKGROUND OF THE INVENTION

There are currently 15.7 million people or 5.9% of the population in the United States who suffer from diabetes mellitus. Each day approximately 2,200 people are diagnosed with diabetes and roughly 798,000 people will be diagnosed this year. Diabetes is the seventh leading cause of death (sixth-leading cause of death by disease) in the United States.

Diabetes mellitus, more commonly known as diabetes, is a disease in which the body does not produce and/or properly use insulin, a hormone that aids the body in converting sugars and other foods into energy. In a non-diabetic individual, insulin is produced in the pancreas at the islets of Langerhans in response to an increase of glucose in the gut and/or blood. Insulin then acts in conjunction with the liver to control glucose metabolism in the body. While diabetes is typically thought of as a blood-sugar disease, diabetes may result in numerous life-threatening complications. For example, diabetes may lead to various microvascular diseases, such as retinopathy, nephropathy, and neuropathy. In the United States, diabetes is the leading cause of new cases of blindness in people ages 20 to 74, is the leading cause of end-stage renal disease, and is the most frequent cause of lower limb amputations. Diabetic individuals also have a higher likelihood of developing life-threatening macrovascular diseases, such as heart disease and stroke.

Several types of diabetes exist. Insulin dependent diabetes mellitus (IDDM), commonly referred to as Type 1 diabetes, is an auto-immune disease that affects the islets of Langerhans, destroying the body's ability to produce insulin. Type 1 diabetes may affect as many as 1 million people in the United States. Non-insulin dependent diabetes mellitus (NIDDM), commonly referred to as Type 2 diabetes, is a metabolic disorder resulting from the body's inability to produce enough insulin or properly use the insulin produced. Roughly 90 percent of all diabetic individuals in the United States suffer from Type 2 diabetes, which is usually associated with obesity and a sedentary lifestyle.

In general, the goal of diabetes treatment is to control glucose level in the blood and maintain it in a range that mimics that of a non-diabetic individual, namely reproduces natural physiological glucose homeostasis. To date, this goal has not been fully effectively achieved.

Diabetes is typically treated by monitoring the glucose level in the body via blood and/or urine sampling and attempting to control the level of glucose in the body using a combination of diet and parenteral injections of insulin. Parenteral injections, such as subcutaneous and intramuscular injections, deliver insulin to the peripheral system. Studies, such as the Diabetes Control and Complications Trial (DCCT), have shown that tight control of blood glucose level to within normal ranges may reduce or eliminate the microvascular complications associated with diabetes. As observed in the DCCT, tight control of blood glucose level may be achievable in some individuals by using three or more daily injections of insulin or by treatment with an insulin pump (continuous subcutaneous insulin infusion). If closely followed, such regimens offer the potential for some control of the disease. However, an increased risk of hypoglycemia was observed in the DCCT when tight control of blood glucose level by peripheral administration was attempted. Additionally, peripheral administration of insulin may result in peripheral hyperinsulinemia, which may increase the risk of various medical complications. Furthermore, many patients may routinely fail to comply with these regimens due to the lack of convenience and/or embarrassment associated with subcutaneous administration of insulin.

In an attempt to overcome the inconvenience and discomfort of subcutaneous administration of insulin, various non-invasive alternatives to injectable insulin have been proposed. For example, U.S. Pat. Nos. 5,320,094 to Laube et al., 5,364,838 to Rubsamen, and 5,997,848 to Patton et al. propose intrapulmonary administration of insulin using inhaler devices. The usefulness of these methods may be limited by the requirement to master the operation of the delivery device, the potential for lung irritation with long-term use, and impaired delivery to those patients with lung disorders. Administration of insulin to the buccal mucosa has also been proposed. While these methods of administration may have been referred to as "oral administration", they are effectively non-injectable forms of peripheral administration with its attendant problems and difficulties.

Delivery of insulin through nasal mucosa by a spray device has also been proposed. These methods resulted in unacceptable levels of intra-patient, dose-to-dose variability of insulin absorption and also resulted in nasal mucosal irritation. As with the intrapulmonary and buccal mucosa methods described above, delivery of insulin through nasal mucosa is a non-injectable form of peripheral administration.

While these non-injectable forms of peripheral administration may avoid the inconvenience of injectable forms, they still suffer from the same risks of peripheral hyperinsulinemia associated with the peripheral injection of insulin. Furthermore, and perhaps most importantly, they do not effectively deliver insulin to the liver. As described above and in more detail in *Goodman & Gilman's, The Pharmacological Basis of Therapeutics* 1487-1507 (9th ed. 1996), insulin acts in conjunction with the liver to control glucose metabolism in the body. To achieve more effective treatment of diabetes mellitus, methods should be provided that mimic the natural delivery of insulin to the liver.

Various methods have been proposed that may attempt to mimic the natural delivery of insulin to the liver. For example, U.S. Pat. No. 4,579,730 to Kidron et al. proposes an enterically-coated pharmaceutical composition for the oral administration of insulin. While this patent asserts that the proposed pharmaceutical formulations have the same effect as naturally secreted insulin on the blood glucose levels, the insulin is not rapidly absorbed from the intestinal lumen into the blood stream. For example, the patent reports at column 4, lines 15-16 that only 5-10% of the insulin is absorbed during 60 minutes. Additionally, this formulation appears to have a limited effect on glucose blood levels within the first hour following administration. (See column 4, Table 1).

As another example, U.S. Pat. No. 4,963,526 to Ecanow proposes an oral dosage form of insulin based upon a two-phase liquid aqueous coacervate system that incorporates the insulin in a coacervate phase of the system. The insulin administered using this formulation does not appear to have a rapid effect on glucose blood levels. For example, at column 9, line 52 through column 10, line 12, the patent reports measuring blood glucose levels three hours after administration and observing blood glucose levels of 66.3% and 47.1% of initial blood levels depending on the dosage given.

As still another example, U.S. Pat. No. 4,863,896 to Geho et al. proposes methods of treating diabetes that utilize a combination of peripherally administered insulin and hepatocyte directed vesicles with encapsulated insulin (HDVI). The HDVI will be taken up only by the liver while the separately administered free insulin will supply the needs of the peripheral system. The patent states that the HDVI may be administered orally; however, no dosage ranges are provided. The co-administration of HDVI and peripheral insulin is required because, unlike naturally produced insulin, none of the HDVI will pass through the liver to the peripheral system. (See column 2, lines 3-14).

As yet another example, U.S. Pat. No. 5,704,910 to Humes proposes an implantable device for delivering a pre-selected molecule, for example, a hormone such as insulin, into a mammals systemic circulation. The patent contemplates anchoring an insulin producing device within the portal vein upstream of (i.e., before) the liver. Reliance on such a device to control the life-threatening disease of diabetes mellitus may be impractical. Furthermore, it is unclear what dosages of insulin would be administered by such a device and precisely how the required dosage would be regulated.

In view of the foregoing, there is a need in the art for methods of treating diabetes mellitus that better mimic the natural delivery of insulin to the liver resulting in improved glucose homeostasis in product administration forms that are convenient and easy to use by patients.

SUMMARY OF THE INVENTION

Embodiments of the present invention provide methods of treating diabetes mellitus that effectively reproduce the natural physiological glucose homeostasis seen in non-diabetics. Unlike the conventional treatment methods described above, methods according to embodiments of the present invention provide for a rapid and effective absorption of insulin into the portal bloodstream. This administration of insulin into the portal bloodstream results in delivery of an effective amount of insulin to the liver; however, unlike the HVDI used in the conventional method described above, some of the insulin provided to the liver is free to pass through the liver to the peripheral system. Thus, methods according to the embodiments of the present invention allow diabetic individuals with healthy livers to metabolize glucose in a way that more closely mimics the natural metabolism of glucose in non-diabetic individuals than any of the conventional methods described above. Methods according to embodiments of the present invention may result in rapid yet controlled drops in blood glucose levels after administration and provide effective control of post-prandial glucose levels. As a result, methods of the present invention may allow diabetic individuals to control blood glucose levels and eliminate or reduce the occurrence of many complications associated with diabetes mellitus. In addition to causing the liver to perform glucose homeostasis, methods of the present invention may also partially or fully engage the liver's role in the regulation of lipid and amino acid metabolism.

According to embodiments of the present invention, a method of treating diabetes mellitus in a patient in need of such treatment includes orally administering an effective amount of insulin drug to the patient in order to treat diabetes mellitus in the patient, wherein the effective amount of insulin durg is administered so that it provides an insulin drug concentration in portal vein blood between about 10 and 1000 µU/ml within 30 minutes of administration.

According to other embodiments of the present invention, the effective amount of insulin drug is between 0.05 and 10 mg per kilogram of patient body weight. The effective amount of insulin drug preferably provides a maximum insulin concentration in peripheral blood within 60 minutes after administration. The effective amount of insulin drug is preferably administered so that peripheral glucose concentration is stabilized. For example, peripheral blood glucose concentration may be within +/−50 percent of an average peripheral glucose concentration measured over a one hour time period beginning within 30 minutes after administration.

According to still other embodiments of the present invention, the effective amount of insulin drug is administered so that average hepatic glucose production measured over 90 minutes after administration is reduced by at least 25 percent when compared to an average hepatic glucose production rate of a diabetic patient without administration. Preferably, this reduction in hepatic glucose production occurs within 30 minutes following administration.

In yet other embodiments of the present invention, the effective amount of insulin drug is administered so that at least 25 percent of the glucose resulting from a meal is hepatically absorbed. Preferably, this absorption occurs within 30 minutes of ingesting the meal. The effective amount of insulin drug is preferably administered less than one hour prior to ingestion of a meal by the patient. The insulin drug is preferably an insulin derivative.

In still other embodiments, the use of the insulin drugs described herein for the preparation of orally administrable medicaments for the treatment of diabetes mellitus is provided.

Methods of the present invention provide for rapid and convenient delivery of insulin to the portal vein and, hence, to the liver. By utilizing methods of the present invention, diabetic individuals may effectively treat both the blood glucose variations and the complications associated with diabetes mellitus.

DETAILED DESCRIPTION OF PREFERRED EMBODIMENTS

Figure 1A:
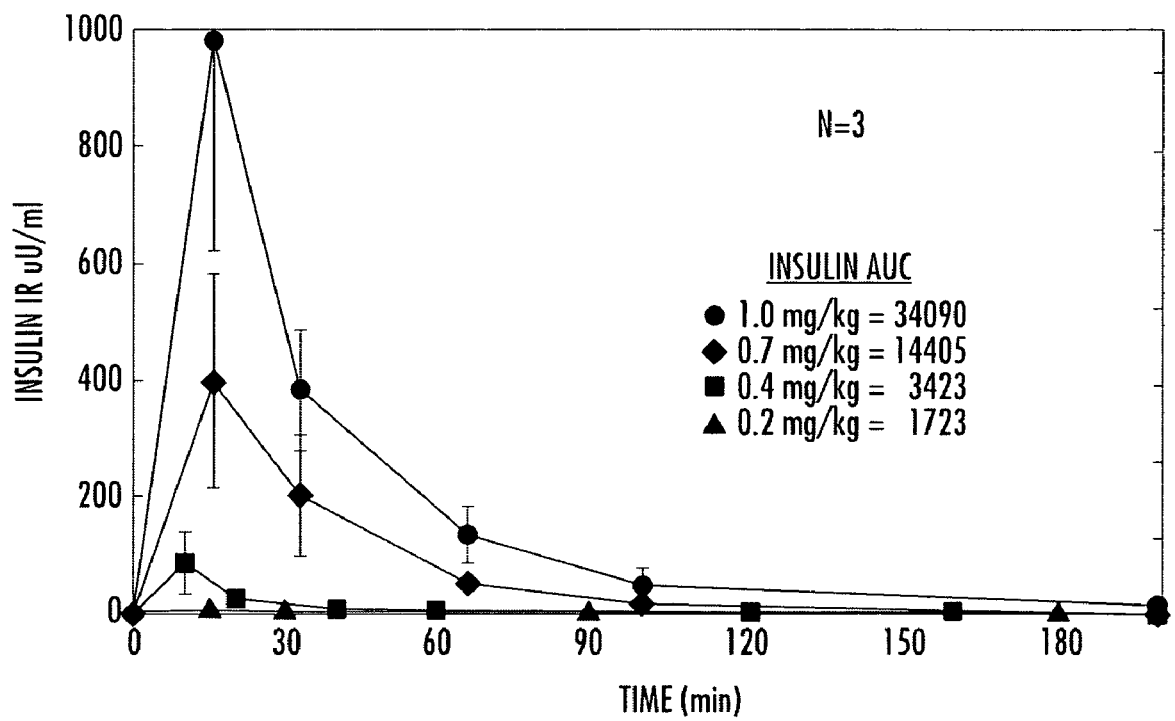
FIG. 1a shows insulin levels in pancreatectomized dogs receiving increasing doses of orally administered HIM2 according to embodiments of the present invention.

The invention will now be described with respect to preferred embodiments described herein. It should be appreciated however that these embodiments are for the purpose of illustrating the invention, and are not to be construed as limiting the scope of the invention as defined by the claims.

In non-diabetic individuals, the pancreas continuously supplies low (or basal) levels of insulin. The liver supplies glucose to the rest of the body when the body is in a fasting state. This is typically referred to as hepatic glucose production. In response to a meal, high levels of insulin are released by the pancreas. The insulin first interacts with the liver, signaling the liver to stop hepatic glucose production and to begin absorbing glucose ingested as part of the meal. Some of the bolus of insulin release by the pancreas passes through the liver and interacts with other body cells, especially muscle, signaling them to absorb and use glucose. Thus, in non-diabetic individuals, the pancreas and the liver work in tandem to provide glucose homeostasis.

Methods according to embodiments of the present invention may restore glucose homeostasis to a diabetic individual having a healthy liver (i.e., a liver capable of normal glucose uptake and production but for the absence of the regulating hormone insulin). By activating the liver to regulate the level of blood glucose, methods of the present invention may reduce or eliminate the hyperglycemia and/or hypoglycemia associated with conventional methods of treatment of diabetes mellitus. Methods according to embodiments of the present invention may also reduce or eliminate some, if not all, of the microvascular complications (e.g., nephropathy, retinopathy and/or neuropathy) and/or macrovascular complications (e.g., myocardial infarction and/or stroke) typically associated with diabetes mellitus. Moreover, methods according to embodiments of the present invention may reduce or eliminate the hyperinsulinemia associated with the peripheral administration (e.g., subcutaneous, intrapulmonary, intranasal, buccal mucosal) of insulin. Furthermore, methods according to embodiments of the present invention may reduce or eliminate the hyperlipidemia associated with diabetes by activating the liver to improve its fatty acid metabolism. Proper activation of the liver may also restore other liver cell, gene-regulated metabolic pathways related to complications associated with diabetes mellitus.

As used herein, the term "insulin drug" refers to any molecule capable of eliciting one or more biological responses associated with insulin (e.g., regulation of glucose homeostasis in target tissues such as the liver, muscle and/or fat, stimulation of cellular utilization and storage of glucose, amino acids, and/or fatty acids, and inhibition of catabolic processes such as the breakdown of glycogen, fat and protein) including, but not limited to, insulin polypeptides such as insulin, insulin analogs, active insulin fragments, and active insulin fragment analogs, insulin polypeptide derivatives, and insulin agonist molecules, mixtures thereof or pharmaceutical compositions comprising such molecules or mixtures of such molecules.

As used herein, the term "insulin" means the insulin of one of the following species: human, cow, pig, sheep, horse, dog, chicken, duck or whale, provided by natural, synthetic, or genetically engineered sources. In various embodiments of the present invention, insulin is preferably human insulin.

As used herein, the term "insulin analog" means insulin wherein one or more of the amino acids have been replaced while retaining some or all of the activity of the insulin. The analog is described by noting the replacement amino acids with the position of the replacement as a superscript followed by a description of the insulin. For example, "$\text{Pro}^{B29}$ insulin, human" means that the lysine typically found at the B29 position of a human insulin molecule has been replaced with proline.

Insulin analogs may be obtained by various means, as will be understood by those skilled in the art. For example, certain amino acids may be substituted for other amino acids in the insulin structure without appreciable loss of interactive binding capacity with structures such as, for example, antigen-binding regions of antibodies or binding sites on substrate molecules. As the interactive capacity and nature of insulin defines its biological functional activity, certain amino acid sequence substitutions can be made in the amino acid sequence and nevertheless remain a polypeptide with like properties.

In making such substitutions, the hydropathic index of amino acids may be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids may be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101, the disclosure of which is incorporated herein in its entirety, provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5) cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As will be understood by those skilled in the art, insulin analogs may be prepared by a variety of recognized peptide synthesis techniques including, but not limited to, classical (solution) methods, solid phase methods, semi-synthetic methods, and recombinant DNA methods.

Examples of human insulin analogs include, but are not limited to, $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ insulin, human; $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; $Ala^{B28}$ $Pro^{B29}$ insulin, human.

As used herein, the term "active insulin fragment" means a segment of the amino acid sequence found in the insulin that retains some or all of the activity of the insulin. Insulin fragments are denoted by stating the position(s) in an amino acid sequence followed by a description of the amino acid. For example, a "B25-B30 human insulin" fragment would be the six amino acid sequence corresponding to the B25, B26, B27, B28, B29 and B30 positions in the human insulin amino acid sequence.

As used herein, the term "active insulin fragment analog" means a segment of the amino acid sequence found in the insulin molecule wherein one or more of the amino acids in the segment have been replace while retaining some or all of the activity of the insulin.

As used herein, "insulin polypeptide derivative" refers to an insulin polypeptide such as insulin, an insulin analog, an active insulin fragment, or an active insulin fragment analog that has been conjugated to one or more moieties, such as acyl moieties (e.g., fatty acids) and/or oligomers, that improve the lipophilicity and/or hydrophilicity of the insulin polypeptide such that the insulin polypeptide conjugate is more lipophilic and/or more hydrophilic than the corresponding unconjugated insulin polypeptide. The hydrophilicity of an insulin polypeptide derivative can be compared to the hydrophilicity of the unconjugated insulin polypeptide by various means as will be understood by those skilled in the art. For example, a given amount of the insulin polypeptide derivative can be added to water, and the resulting solution can be mixed and filtered. The filtrate can be analyzed using known HPLC methods to determine the amount of conjugate present in the filtrate, and, thus, the amount of conjugate dissolved in the water. Alternatively, the filter paper can be weighed before and after filtration to determine the weight of conjugate not dissolved in the water. This weight can be used to determine the concentration of conjugate in the water. The same procedure can be repeated using the unconjugated insulin polypeptide and the two concentrations can be compared. The molecule that produces the higher concentration in water is considered to be the more hydrophilic molecule. The lipophilicity of an insulin polypeptide derivative can be compared to the lipophilicity of the unconjugated insulin polypeptide by various means as will be understood by those skilled in the art. For example, a given amount of the insulin polypeptide derivative can be analyzed by reverse phase HPLC as will be understood by those skilled in the art. The unconjugated insulin polypeptide can be analyzed using the same reverse phase HPLC method, and the elution times of the insulin polypeptide derivative and the unconjugated insulin polypeptide can be compared. The molecule with the longer elution time is considered to be the more lipophilic molecule.

As used herein, the term "amphiphilically balanced insulin polypeptide-oligomer conjugate" refers to a conjugate that is both more lipophilic than the unconjugated insulin polypeptide and more hydrophilic than the unconjugated insulin polypeptide. One skilled in the art will understand how to determine if an insulin polypeptide-oligomer conjugate is amphiphilically balanced. For example, a given amount of the insulin polypeptide-oligomer conjugate can be added to water, and the resulting solution can be mixed and filtered. The filtrate can be analyzed using known HPLC methods to determine the amount of conjugate present in the filtrate, and, thus, the amount of conjugate dissolved in the water. Alternatively, the filter paper can be weighed before and after filtration to determine the weight of conjugate not dissolved in the water. This weight can be used to determine the concentration of conjugate in the water. The concentration of insulin polypeptide-oligomer conjugate in the water should be greater than the concentration in water of unconjugated insulin polypeptide determined utilizing the same procedure. A given amount of the insulin polypeptide-oligomer conjugate can then be analyzed by reverse phase HPLC as will be understood by those skilled in the art. The elution time of the insulin polypeptide-oligomer conjugate should be greater than the elution time of the unconjugated insulin polypeptide.

As used herein, the term "portal administration" means administration of all or substantially all of a given dose to the portal vein. Portal administration may be achieved by various administration routes including, but not limited to, oral administration, subcutaneous administration into the peritoneal cavity, rectal administration, and direct infusion into the portal vein.

As used herein, the term "peripheral administration" means administration of all or substantially all of a given dose to the peripheral system. Peripheral administration may be achieved by various administration routes including, but not limited to, intrapulmonary, intranasal, via the buccal mucosa, and parenteral injections (e.g., subcutaneous and intramuscular injections).

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—CH$_2$—CH$_2$—O—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

As used herein, phrases such as "between X and Y" should be interpreted to include X and Y.

As used herein, phrases such as "between about X and Y" mean "between about X and about Y" and phrases such as "from about X to Y" mean "from about X to about Y."

As used herein, the terms "ester moiety", "thio-ester moiety", "carbamate moiety", "ether moiety", "thio-carbamate moiety", "carbonate moiety", "thio-carbonate moieties", "urea moiety" and "amide moiety" are used to refer to the named moiety, in any of its various possible orientations. The moiety may include one or two lower alkylene moieties in addition to the named moiety. For example, the term "ester moiety" refers to a —O—C(O)— moiety, a —C(O)—O— moiety, or either of these moieties having a lower alkylene moiety at one or both ends of the moiety.

According to embodiments of the present invention, a method of treating diabetes mellitus in a patient in need of such treatment includes orally administering an effective amount of an insulin drug to the patient in order to treat diabetes mellitus in the patient, where the effective amount of insulin drug is administered so that it provides an insulin drug concentration in portal vein blood between about 10, 200 or 400 and 600, 800 or 1000 µU/ml within about 60 minutes of administration, more preferably within about 15 or 30 minutes of administration. Methods according to the present invention may provide concentrations of insulin drug in the bloodstream that are up to 100 times the basal levels of insulin normally present.

The effective amount of insulin drug is preferably between about 0.05, 0.1, 0.15 or 0.2 and 2, 5 or 10 mg per kilogram of patient body weight. More preferably, the effective amount of insulin drug is between about 0.3 and 1 mg per kilogram of patient body weight. When the dosage of insulin drug is too low, desirable activation of the liver is not achieved. When the dosage is too high, an excessive amount of insulin drug may pass through the liver into the peripheral system potentially resulting in a hypoglycemic condition.

According to embodiments of methods of the present invention, oral administration of an effective amount of an insulin drug preferably provides rapid drops in fasting peripheral blood glucose concentrations. Peripheral blood glucose concentrations preferably drop by about 10, 15, or 25 percent within about 5, 15, or 30 minutes following administration.

Methods according to embodiments of the present invention preferably provide for rapid delivery of insulin drug to the peripheral system. Oral administration of an effective amount of the insulin drug provides a maximum insulin concentration in peripheral blood preferably within about 60 minutes after administration, more preferably within about 30 minutes after administration, and still more preferably within about 15 minutes after administration. Rapidly achieving a maximum glucose concentration counteracts an upsurge of post-prandial glucose mimicking the natural pancreatic pattern of release of insulin at mealtime. The administered insulin drug preferably clears the bloodstream within about 3 or 4 hours, and, more preferably, clears the bloodstream within about 2 hours.

According to embodiments of methods of the present invention, oral administration of an effective amount of insulin drug stabilizes the peripheral glucose concentration. For example, by employing methods of the present invention, the peripheral blood glucose concentration may be maintained within +/− about 5, 10, 20 or 50 percent of an average peripheral glucose concentration. The average peripheral glucose concentration may be determined over about a 30, 60, 90, or 240 minute time period beginning within about 15, 30 or 60 minutes after administration.

In still other embodiments of the present invention, methods of orally administering insulin to a patient suffering from diabetes mellitus reduce the hepatic glucose production of the patient. The hepatic glucose production is preferably reduced by at least about 25, 35, 50, 75, 90, or 95 percent when compared to hepatic glucose production of the patient without administration, and is most preferably reduced by about 100 percent when compared to hepatic glucose production of the patient without administration. This reduction in hepatic glucose production preferably occurs within about 30, 60 or 90 minutes following administration. Hepatic glucose production is preferably determined by measuring peripheral glucose levels over a period of time when peripheral insulin levels are at or near basal levels. The period of time is preferably between about 1 and 4 hours, more preferably between about 1 and 2 hours, and most preferably about 1.5 hours.

According to other embodiments of the present invention, oral administration of an effective amount of insulin controls a rise in glucose typically associated with ingesting a meal (i.e., the post-prandial rise in glucose). The post-prandial rise in glucose may be partially or completely controlled by methods of the present invention. Preferably, at least about 25 percent of post-prandial glucose is hepatically absorbed, more preferably at least about 40 percent is absorbed, and, still more preferably, at least about 55 percent is absorbed. The post-prandial glucose absorption preferably occurs within about 120 minutes of ingesting the meal, and more preferably occurs within about 15 or 30 minutes of ingesting the meal.

Oral administration of the insulin drug may occur at various times during the day. The insulin drug is preferably administered at or near (e.g., within one hour of) meal time. In embodiments of the present invention, the insulin drug is administered less than about one hour before ingesting a meal. The insulin drug is preferably administered less than about 30 minutes prior to ingesting a meal, and is more preferably administered less than about 20 minutes prior to ingesting a meal. In other embodiments of the present invention, the insulin drug is administered less than one hour after ingesting a meal, and is preferably administered less than about 30 minutes after ingesting a meal. In still other embodiments, the insulin drug is administered at the same time as ingesting a meal. Insulin drug administered at the same time as ingesting the meal may be less preferred because it may require higher dosages and result in dose-to-dose variability for a given patient.

Administration of the insulin drug may occur before one or more meals per day. Additionally, the insulin drug may be administered at various times in addition to a meal time, for example, before retiring for four or more hours of sleep (e.g., going to bed at night) and/or upon waking up from four or more hours of sleep (e.g., waking up in the morning). Administration of insulin drug according to methods of the present invention prior to retiring for four or more hours of sleep may provide effective glucose homeostasis throughout all or a portion of the period of sleep, preventing or reducing the likelihood of the Dawn Phenomenon, which typically occurs in individuals with Type 1 diabetes mellitus and is characterized by a hypoglycemic episode occurring during a period of sleep.

According to embodiments of the present invention, an insulin drug is preferably administered at appropriate dosages and frequencies so as to achieve and/or maintain activation of the liver such that it performs glucose homeostasis. For example, the insulin drug may be administered uninterruptedly (i.e., administered at least once per day) or cyclically (i.e., administered for one or more consecutive days followed by one or more consecutive days without administration). Uninterrupted administration may be desirable when it is necessary to administer one or more dose per day in order to achieve and/or maintain the activity of the liver in controlling/helping to control glucose levels in the bloodstream. When uninterrupted administration is employed, it may be possible to utilize lower dosages of insulin.

Cyclical administration may be desirable when the activity of the liver persists over one or more days following administration of insulin. For example, the insulin drug may be administered for one or more days followed by a period of one or more days when the insulin drug is not administered. The cyclical administration need not follow a uniform administration pattern. For example, a cyclical administration regimen may employ four days of administration followed by one day without administration followed by two days of administration followed by three days without administration. Cyclical administration may be utilized to treat Type 1 and Type 2 diabetes mellitus; however, cyclical administration may be most beneficial in the treatment of Type 2 diabetes mellitus.

In other embodiments according to the present invention, methods of treating diabetes mellitus in a patient in need thereof comprise orally administering an effective amount of a first insulin drug to the patient as described in the various embodiments above and administering an effective amount of a second insulin drug to the peripheral system of the patient. Preferably, the peripheral administration is performed by parenteral injection. More preferably, the peripheral administration is performed by continuous subcutaneous insulin injection (CSII), as will be understood by those skilled in the art. The CSII dosage is preferably selected to provide a basal level of insulin in the body. The CSII dosage may be between about 0.1 and 3 Units (U) per hour, and is preferably between about 0.5 and 1.5 U/hour. The first and second insulin drugs may be the same or different.

In still other embodiments according to the present invention, methods of treating diabetes mellitus in a patient in need thereof comprise orally administering an effective amount of a first insulin drug to the patient as described in the various embodiments above and continuously administering a basal amount of a second insulin drug to the portal vein. This administration may be accomplished by CSII that is administered to the peritoneal cavity. It is believed that these methods of the present invention may mimic the bolus of insulin introduced into the portal vein by the pancreas of a non-diabetic individual following ingestion of a meal as well as mimicking the basal level of insulin provided by the pancreas on a continuous basis in non-diabetic individuals. The first insulin drug and the second insulin drug may be the same or different.

The insulin drug of the above-described embodiments is preferably an insulin polypeptide derivative. The insulin polypeptide derivative is preferably an acylated insulin polypeptide or an insulin polypeptide-oligomer conjugate. Acylated insulin polypeptides are insulin polypeptides that have been derivatized with one or more acyl-containing moieties, such as fatty acid moieties and/or arylacyl moieties. The fatty acid moiety may be a saturated or unsaturated, linear or branched fatty acid moiety such as, but not limited to, caproic acid, caprylic acid, capric acid, undecanoic acid, lauric acid, tridecanoic acid, myristic acid, pentadecanoic acid, palmitic acid, heptadecanoic acid, stearic acid, oleic acid, elaidic acid, linoleic, linolenic, arachidic, and arachidonic acid, or a fatty acid derivative such as an aryl-fatty acid derivative (e.g., phenylacetyl) or a cycloalkyl-fatty acid derivative (e.g., cyclohexylacetyl or cyclohexylpropionyl). Arylacyl moieties include, but are not limited to, benzoyl. The insulin polypeptide-oligomer conjugate is an insulin polypeptide conjugated with an oligomer, such as a polyalkylene glycol moiety or a polyalkylene glycol-containing moiety. Insulin polypeptide derivatives according to embodiments of the present invention may be synthesized using methods that are known to those skilled in the art.

According to embodiments of the present invention, the insulin polypeptide-oligomer conjugate is an amphiphilically balanced insulin polypeptide-oligomer conjugate. The amphiphilically balanced insulin polypeptide-oligomer conjugate preferably comprises an insulin polypeptide coupled to an oligomer that comprises a hydrophilic moiety coupled to a lipophilic moiety. The insulin polypeptide is preferably insulin or an insulin analog. More preferably, the insulin polypeptide is human insulin or a human insulin analog. Still more preferably, the insulin polypeptide is human insulin. The hydrophilic moiety may be coupled to the lipophilic moiety by a hydrolyzable or a non-hydrolyzable bond, or there may be one or more intervening moieties that couple the hydrophilic moiety to the lipophilic moiety.

The hydrophilic moiety of the amphiphilically balanced insulin polypeptide-oligomer conjugate is a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety is preferably a polyalkylene glycol moiety. The polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

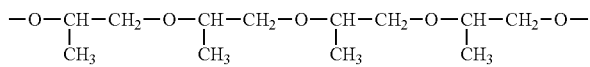

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

The lipophilic moiety of the amphiphilic insulin polypeptide-oligomer conjugate is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22 carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, myristate, palmitate, stearate, arachidate, behenate, lignocerate, and cerotate.

The oligomer portion of the amphiphilically balanced insulin polypeptide-oligomer conjugate may comprise one or more other moieties as will be understood by those skilled in the art including, but not limited to, additional hydrophilic moieties, spacer moieties, linker moieties, and terminating moieties. The various moieties in the oligomer are covalently coupled to one another by either hydrolyzable or non-hydrolyzable bonds.

The oligomer portion of the amphiphilically balanced insulin polypeptide-oligomer conjugate may comprise one or more additional hydrophilic moieties (i.e., moieties in addition to the hydrophilic moiety) including, but not limited to, sugars, polyalkylene glycols, and polyamine/PEG copolymers. Adjacent polyalkylene glycol moieties will be considered to be the same moiety if they are coupled by ether bonds. For example, the moiety

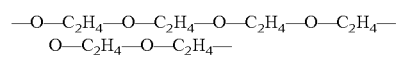

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

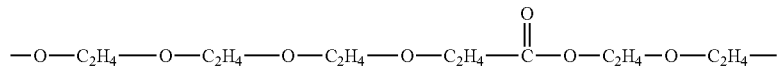

is a polyethylene glycol moiety having four polyethylene glycol subunits and an additional hydrophilic moiety having two polyethylene glycol subunits. Preferably, oligomers according to embodiments of the present invention comprise a polyalkylene glycol moiety and no additional hydrophilic moieties.

The oligomer portion of the amphiphilically balanced insulin polypeptide-oligomer conjugate may comprise one or more spacer moieties as will be understood by those skilled in the art. Spacer moieties may, for example, be used to separate a hydrophilic moiety from a lipophilic moiety, to separate a lipophilic moiety or hydrophilic moiety from the insulin polypeptide, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

The oligomer portion of the amphiphilically balanced insulin polypeptide-oligomer conjugate may comprise one or more linker moieties that are used to couple the oligomer with the insulin polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

The oligomer portion of the amphiphilically balanced insulin polypeptide-oligomer conjugate may comprise one or more terminating moieties at the one or more ends of the oligomer, which are not coupled to the insulin polypeptide.

The terminating moiety is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to other embodiments of the present invention, the insulin drug administered according to the methods of treating diabetes mellitus in a patient in need of such treatment described above is an insulin polypeptide-oligomer conjugate comprising the structure of Formula I:

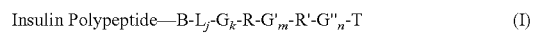

Insulin Polypeptide—B-L$_j$-G$_k$-R-G'$_m$-R'-G''$_n$-T    (I)

wherein:
B is a bonding moiety;
L is a linker moiety;
G, G' and G" are individually selected spacer moieties;
R is a lipophilic moiety and R' is a polyalkylene glycol moiety, or R' is the lipophilic moiety and R is the polyalkylene glycol moiety;
T is a terminating moiety; and
j, k, m and n are individually 0 or 1.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula I is preferably an amphiphilically balanced insulin polypeptide-oligomer conjugate.

According to these embodiments of the present invention, the polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

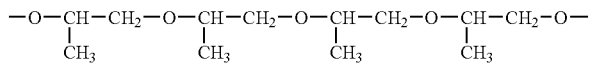

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22 carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaenoate, and docosahexaenoate; and saturated fatty acid moieties such as acetate, caproate, caprylate, caprate, laurate, myristate, palmitate, stearate, arachidate, behenate, lignocerate, and cerotate.

According to these embodiments of the present invention, the spacer moieties, G, G' and G", are spacer moieties as will be understood by those skilled in the art. Spacer moieties are preferably selected from the group consisting of sugar moieties, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms. Preferably, oligomers of these embodiments do not include spacer moieties (i.e., k, m and n are preferably 0).

According to these embodiments of the present invention, the bonding moiety, B, may be various bonding moieties as will be understood by those skilled in the art including, but not limited to, an ester moiety, a thio-ester moiety, an ether moiety, a carbamate moiety, a thio-carbamate moiety, a carbonate moiety, a thio-carbonate moiety, an amide moiety, a urea moiety, and a covalent bond. When the bonding moiety is a carbamate moiety or an amide moiety, the nitrogen portion of the moiety is preferably provided by an amino moiety of the insulin polypeptide, such as the e-amino moiety at the $Lys^{B29}$ position of human insulin. The bonding moiety is preferably an ester moiety, an ether moiety, a carbamate moiety, a carbonate moiety, an amide moiety, or a covalent bond. The bonding moiety is more preferably an ester moiety, a carbamate moiety, a carbonate moiety, or an amide moiety. The bonding moiety is still more preferably an amide moiety having the nitrogen portion of the amide moiety provided by an amino moiety of the insulin polypeptide.

According to these embodiments of the present invention, the linker moiety, L, may be various linker moieties as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

According to these embodiments of the present invention, the terminating moiety, T, is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugar moieties, cholesterol, alcohols, and fatty acid moieties.

In still other embodiments, the insulin drug administered according to the methods of treating diabetes mellitus in a patient in need of such treatment described above is an insulin polypeptide-oligomer conjugate comprising the structure of Formula II:

$$\text{Insulin polypeptide} - X(CH_2)_m Y(C_2H_4O)_n R \quad \text{(II)}$$

wherein:

X is an ester moiety, a thio-ester moiety, an ether moiety, a carbamate moiety, a thio-carbamate moiety, a carbonate moiety, a thio-carbonate moiety, an amide moiety, a urea moiety or a covalent bond; is preferably an ester moiety, an ether moiety, a carbamate moiety, a carbonate moiety, an amide moiety, or a covalent bond; is more preferably an ester moiety, a carbamate moiety, a carbonate moiety, or an amide moiety; and is still more preferably an amide moiety. When X is an amide moiety or a carbamate moiety, an amino group of the insulin polypeptide is preferably the nitrogen portion of the amide or carbamate moiety;

Y is an ester moiety, a thio-ester moiety, an ether moiety, a carbamate moiety, a thio-carbamate moiety, a carbonate moiety, a thio-carbonate moiety, an amide moiety, a urea moiety or a covalent bond, is preferably an ester moiety, an ether moiety, a carbamate moiety, a carbonate moiety, an amide moiety, or a covalent bond; is more preferably an ester moiety, an ether, a carbamate moiety, a carbonate moiety, or an amide moiety; and is still more preferably an ether moiety.

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The sugar moiety may be various sugar moieties as will be understood by those skilled in the art. Likewise, the alcohol moiety may be various alcohol moieties as will be understood by those skilled in the art.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula II is preferably an amphiphilically balanced insulin polypeptide-oligomer conjugate.

In still other embodiments, the insulin drug administered according to the methods of treating diabetes mellitus in a patient in need of such treatment described above is an insulin polypeptide-oligomer conjugate comprising the structure of Formula III:

wherein:

X is an ester moiety, a thio-ester moiety, an ether moiety, a carbamate moiety, a thio-carbamate moiety, a carbonate moiety, a thio-carbonate moiety, an amide moiety, a urea moiety or a covalent bond; is preferably an ester moiety, an ether moiety, a carbamate moiety, a carbonate moiety, an amide moiety, or a covalent bond; is more preferably an ester moiety, a carbamate moiety, a carbonate moiety, or an amide moiety; and is still more preferably an amide moiety. When X is an amide moiety or a carbamate moiety, an amino group of the insulin polypeptide is preferably the nitrogen portion of the amide or carbamate moiety.

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The sugar moiety may be various sugar moieties as will be understood by those skilled in the art. Likewise, the alcohol moiety may be various alcohol moieties as will be understood by those skilled in the art.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula III is preferably an amphiphilically balanced insulin polypeptide-oligomer conjugate.

In yet other embodiments, the insulin drug administered according to the methods of treating diabetes mellitus in a patient in need of such treatment described above is an insulin polypeptide-oligomer conjugate comprising the structure of Formula IV:

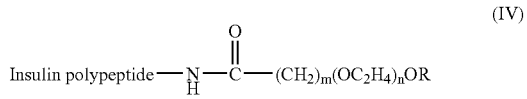

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The sugar moiety may be various sugar moieties as will be understood by those skilled in the art. Likewise, the alcohol moiety may be various alcohol moieties as will be understood by those skilled in the art.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula IV is preferably an amphiphilically balanced insulin polypeptide-oligomer conjugate.

In still other embodiments, the insulin drug administered according to the methods of treating diabetes mellitus in a patient in need of such treatment described above is an insulin polypeptide-oligomer conjugate comprising the structure of Formula V:

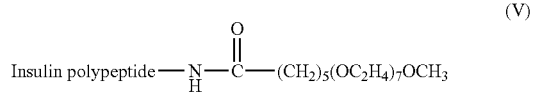

According to these embodiments of the present invention, the insulin polypeptide is preferably insulin or an insulin analog. More preferably, the insulin polypeptide is human insulin or a human insulin analog, and, still more preferably, the insulin polypeptide is human insulin. When the insulin polypeptide in the structure of Formula V is human insulin and the oligomer is conjugated to the B29 lysine of the human insulin, this insulin-oligomer conjugate is referred to herein as HIM2. HIM2 is a polydispersed mixture of insulin-oligomer conjugates. It may be still more preferable to use a substantially monodispersed or monodispersed mixture of insulin-oligomer conjugates as described in U.S. Pat. No. 6,828,297 issued Dec. 7, 2004, to Ekwuribe et al. The insulin polypeptide-oligomer conjugate of Formula V is amphiphilically balanced when the insulin polypeptide is insulin.

HIM2 may be synthesized by various methods as will be understood by those skilled in the art. HIM2 is preferably synthesized utilizing proinsulin as a starting material as described in U.S. Pat. No. 6,913,903 issued Jul. 5, 2005, to Soltero et al. For example, HIM2 has been synthesized as follows. Recombinant proinsulin having a leader peptide (MW 10,642 Daltons) was obtained from Biobras, of Belo Horizonte, Brazil. A $2.32 \times 10^{-3}$ mmol portion of the proinsulin was dissolved in 10 mL of DMSO. To the solution was added 324 µL of triethylamine. The resulting solution was allowed to stir for 5 minutes, and then a solution of activated methylheptaethylene glycol ((PEG7)-hexyl oligomer) ($9.30 \times 10^{-3}$ mmol) in acetonitrile was added. The course of the conjugation (acylation) reaction was monitored by HPLC. When reaction appeared to be complete, it was quenched by addition of 3.54 mL of 5% aqueous trifluoroacetic acid solution. The reaction mixture was then processed and exchanged into 100 mM Tris-HCl Buffer, pH 7.6 to provide a product mixture. An aliquot of the Tris-HCl solution of the product mixture was analyzed by HPLC to determine the polypeptide concentration. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (0.424 µmol/mL) was then allowed to react with trypsin ($5.97 \times 10^{-4}$ µmol/mL) and carboxypeptidase B ($1.93 \times 10^{-4}$ µmol/mL). After 30 minutes, the reaction was quenched by the addition of 1.58 mL of 1% trifluoroacetic acid in acetonitrile. The major products were identified by HPLC retention time (relative to the retention times of known reference standards) and mass spectral analysis. Insulin (10%) and Lys$^{B29}$-Hexyl-PEG7-Oligomer-Conjugated Insulin (84%) were thus obtained.

In the various embodiments of insulin polypeptide-oligomer conjugates described above, the oligomer is covalently coupled to the insulin polypeptide. In some embodiments, the oligomer is coupled to the insulin polypeptide utilizing a hydrolyzable bond (e.g., an ester or carbonate bond). A hydrolyzable coupling may provide an insulin polypeptide-oligomer conjugate that acts as a prodrug. In other embodiments, the oligomer is coupled to the insulin polypeptide utilizing a non-hydrolyzable bond (e.g., a carbamate, amide, or ether bond).

The insulin polypeptide-oligomer conjugates employed in the various embodiments described above may be synthesized by various methods as will be understood by those skilled in the art. For example, polydispersed insulin polypeptide-oligomer conjugates may be synthesized by the methods provided in one or more of the following references: U.S. Pat. No. 5,359,030 to Ekwuribe; U.S. Pat. No. 5,438,040 to Ekwuribe; U.S. Pat. No. 5,681,811 to Ekwuribe; U.S. Pat. No. 6,309,633 to Ekwuribe et al.; and U.S. Pat. No. 6,913,903 issued Jul. 5, 2005 to Soltero et al., the disclosures of which are incorporated herein by reference in their entireties. Non-polydispersed (e.g., substantially monodispersed and monodispersed) insulin polypeptide-oligomer conjugates may be synthesized by methods provided in one or more of the following references: U.S. Pat. No. 6,858,850 issued Feb. 22, 2005, to Ekwuribe et al.; U.S. Pat. No. 6,828,297 issued Dec. 7, 2004 to Ekwuribe et al.; U.S. Pat. No. 6,913,903 issued Jul. 5, 2005, to Soltero et al., the disclosures of which are incorporated herein by reference in their entireties. Oligomers according to embodiments of the present invention are preferably substantially monodispersed and are more preferably monodispersed.

A monodispersed mixture of insulin polypeptide-oligomer conjugates may be synthesized, for example, utilizing methods described in U.S. Pat. No. 5,359,030 to Ekwuribe; U.S. Pat. No. 5,438,040 to Ekwuribe; U.S. Pat. No. 5,681,811 to Ekwuribe; or U.S. Pat. No. 6,309,633 to Ekwuribe et al. by using a monodispersed polyethylene glycol (PEG) mixture as a starting material. Such monodispersed PEG mixtures may be provided, for example, by methods described in Yiyan Chen & Gregory L. Baker, *Synthesis and Properties of ABA Amphiphiles*, 64 *J. Org. Chem.* 6870-6873 (1999) and in Gérard Coudert et al., *A Novel, Unequivocal Synthesis of Polyethylene Glycols*, Synthetic Communications, 16(1): 19-26 (1986). A preferred method of synthesizing monodispersed PEG mixtures to be utilized in forming monodispersed mixtures of insulin polypeptide-oligomer conjugates includes reacting a monodispersed mixture of compounds having the structure of Formula I:

wherein R' is H or a lipophilic moiety; n is from 1 to 25; and X$^+$ is a positive ion, with a monodispersed mixture of compounds having the structure of Formula II:

wherein R$^2$ is H or a lipophilic moiety; and m is from 1 to 25, under conditions sufficient to provide a monodispersed mixture of polymers comprising polyethylene glycol moieties and having the structure of Formula III:

$$R^2(OC_2H_4)_{m+n}\text{—}OR^1 \quad\quad (III).$$

Figure 14:
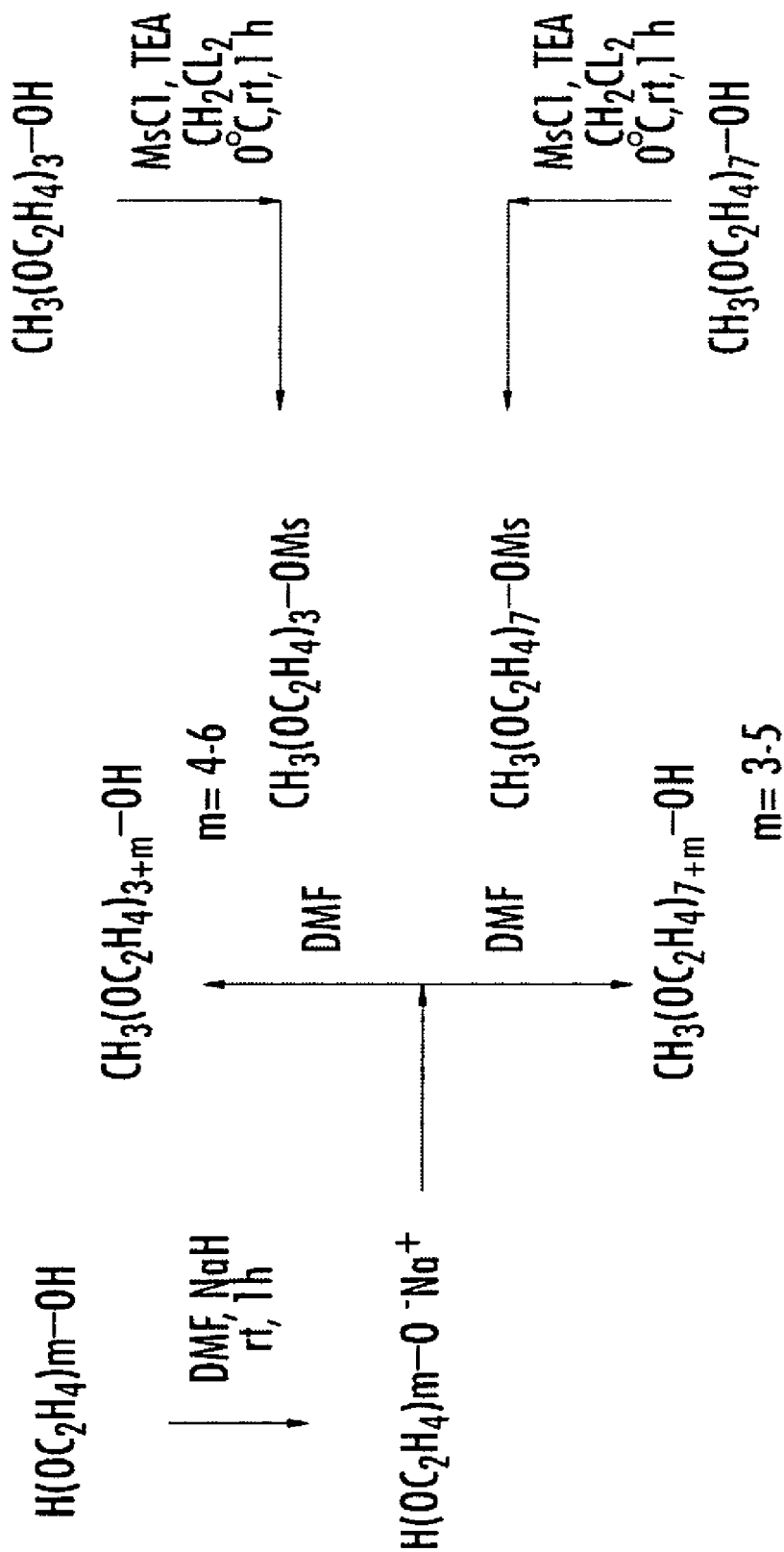
FIG. 14 shows a reaction scheme for providing monodispersed mixtures of polyethylene glycol.
Figure 15:
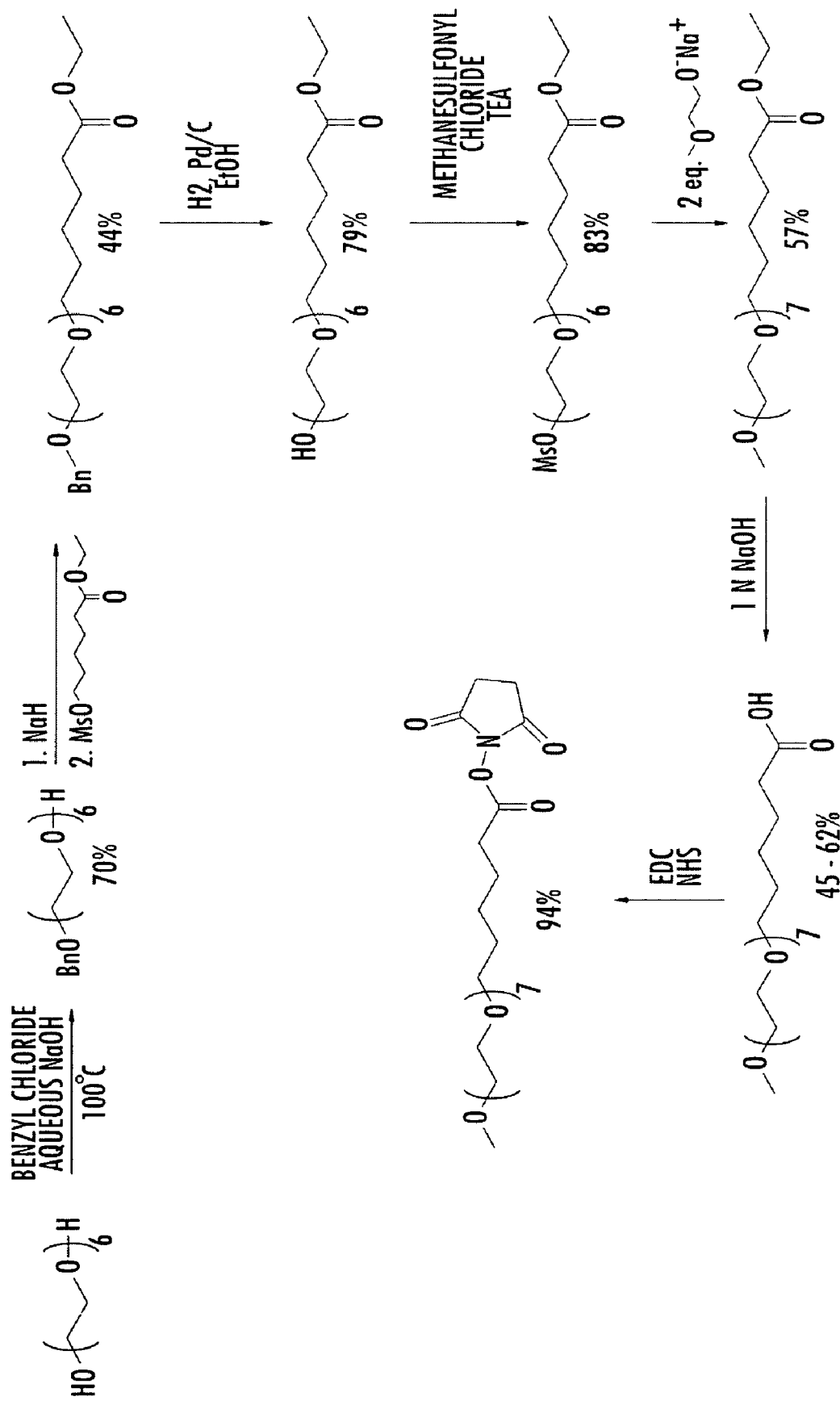
FIG. 15 shows a reaction scheme for providing monodispersed mixtures of an oligomer comprising a polyethylene glycol moiety.

Exemplary reaction schemes are provided in FIGS. 14 and 15.

The methods according to embodiments of the invention described above can be carried out utilizing a pharmaceutical composition comprising an insulin drug as described above and a pharmaceutical carrier. The carrier must, of course, be acceptable in the sense of being compatible with any other ingredients in the pharmaceutical composition and should not be deleterious to the subject. The carrier may be a solid or a liquid, or both, and is preferably formulated with the insulin drug as a unit-dose formulation, for example, a tablet, which may contain from about 0.01 or 0.5% to about 95% or 99% by weight of the insulin drug. The pharmaceutical compositions may be prepared by any of the well-known techniques of pharmacy including, but not limited to, admixing the components, optionally including one or more accessory ingredients. See, e.g., Remington, *The Science And Practice of Pharmacy* (9th Ed. 1995).

Pharmaceutical compositions suitable for oral administration may be presented in discrete units, such as capsules, cachets, lozenges, or tables, each containing a predetermined amount of the mixture of insulin drug-oligomer conjugates; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the insulin drug and a suitable carrier (which may contain one or more accessory ingredients as noted above).

In addition to an insulin drug, solid pharmaceutical compositions for oral administration according to embodiments of methods of the present invention may comprise various other ingredients as will be understood by those skilled in the art including, but not limited to, one or more of the ingredients described in the *National Formulary* 19, pages 2404-2406 (2000), the disclosure of pages 2404 to 2406 being incorporated herein by reference in their entirety. For example, the solid pharmaceutical formulations may include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers that may be used encompass those that are known in the art and are useful in the manufacture of various dosage forms. If desired, the solid formulations may include other components such as bulking agents and/or granulating agents, and the like. Solid pharmaceutical compositions may be provided by various methods as will be understood by those skilled in the art.

Solid dosage units for oral administration according to embodiments of methods of the present invention may be prepared by various methods as will be understood by those skilled in the art. For example, the insulin drug may be mixed with a solid, pulverant carrier such as, for example, lactose, saccharose, sorbitol, mannitol, starch, amylopectin, cellulose derivatives or gelatin, as well as with an antifriction agent such as, for example, magnesium stearate, calcium stearate, and polyethylene glycol waxes. The mixture may then be pressed into tablets. Tablets for oral use may also be prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is pressed through a stainless steel sieve having a desired size. The layers of the mixture are then dried in controlled drying units for determined length of time to achieve a desired particle size and consistency. The granules of the dried mixture are sieved to remove any powder. To this mixture, disintegrating, anitfriction, and anti-adhesive agents are added. Finally, the mixture is pressed into tablets using a machine with the appropriate punches and dies to obtain the desired tablet size. The operating parameters of the machine may be selected by the skilled artisan.

If coated tablets are desired, the above prepared cores may be coated with a concentrated solution of sugar, which may contain gum arabic, gelatin, talc, titanium dioxide, or with a lacquer dissolved in volatile organic solvent or mixture of solvents. Additionally, coating may be carried out in aqueous or nonaqueous media using various excipients including, but not limited to, dispersed methylcellulose, dispersed ethylcellulose, dispersed methacrylates or mixtures thereof. To this coating various dyes may be added in order to distinguish among tablets with different active compounds or with different amounts of the active compound present.

Soft gelatin capsules may be prepared in which capsules contain a mixture of the active ingredient and a liquid, such as vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

Dry powder capsules may be made by various methods understood by those skilled in the art. An embodiment of a dry powder capsule that may be orally administered according to embodiments of the present invention is as follows:

| Component | % (w/w) |
| --- | --- |
| HIM2 | 1.11 |
| sodium cholate | 13.29 |
| capric acid | 5.13 |
| lauric acid | 5.13 |
| tris(hydroxymethy)aminomethane | 41.04 |
| sodium phosphate | 30.97 |
| sodium hydroxide | 1.03 |

Liquid pharmaceutical compositions that may be orally administered according to embodiments of methods of the present invention may be various liquid pharmaceutical compositions that include the insulin drug as an active ingredient as will be understood by those skilled in the art including, but not limited to, solutions or suspensions in aqueous or non-aqueous liquids, and oil-in-water or water-in-oil emulsions. In addition to the active insulin drug, the liquid pharmaceutical formulation may comprise various ingredients including, but not limited to, absorption enhancers, buffering agents, polyhydric alcohols, polyalkylene oxides, and flavoring agents.

Absorption enhancers may be various absorption enhancers as will be understood by those skilled in the art including, but not limited to, bile acids such as, but not limited to, cholic acid, deoxycholic acid, ursodeoxycholic acid, lithocholic acid, and taurocholic acid and/or the pharmaceutically acceptable salts (e.g., earth metal salts) thereof, and fatty acids such as, but not limited to, caproic acid, caprylic acid, capric acid, undecanoic acid, lauric acid, tridecanoic acid, myristic acid, pentadecanoic acid, palmitic acid, heptadecanoic acid, stearic acid, oleic acid, elaidic acid, linoleic acid, linolenic acid, arachidic acid, arachidonic acid, and mixtures thereof.

Buffering agents may be various buffering agents as will be understood by those skilled in the art including, but not limited to, tris(hydroxymethyl)aminomethane, triethanolamine, sodium phosphate, citric acid, and mixtures thereof.

Polyhydric alcohols may be various polyhydric alcohols as will be understood by those skilled in the art including, but not limited to, glycerol. Polyalkylene glycols may be various polyalkylene glycols as will be understood by those skilled in the art including, but not limited to, polyethylene glycol and polypropylene glycol.

Flavoring agents may be various flavoring agents as will be understood by those skilled in the art including, but not limited to, natural or artificial flavors and sweeteners.

Embodiments of liquid pharmaceutical formulations that may be orally administered according to embodiments of methods of the present invention include the following:

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| tris(hydroxymethy)aminomethane | 250 | mM | 3.03 |
| sodium phosphate | 250 | mM | 3.00 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| tris(hydroxymethy)aminomethane | 500 | mM | 6.05 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| tris(hydroxymethy)aminomethane | 250 | mM | 3.03 |
| triethanolamine | 250 | mM | 3.73 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| citric acid | 500 | mM | 9.60 |
| triethanolamine | 250 | mM | 3.73 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| citric acid | 500 | mM | 9.60 |
| tris(hydroxymethy)aminomethane | 250 | mM | 3.03 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| citric acid | 500 | mM | 9.60 |
| sodium phosphate | 250 | mM | 3.00 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 2 | % | 2.00 |
| citric acid | 350 | mM | 6.72 |
| tris(hydroxymethy)aminomethane | 350 | mM | 4.24 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| lauric acid | 2 | % | 2.00 |
| citric acid | 350 | mM | 6.72 |
| triethanolamine | 350 | mM | 4.24 |
| sucralose | 0.2 | % | 0.20 |
| strawberry flavor | 0.4 | % | 0.4 |
| propylene glycol | 20 | % | 20.00 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 1 | % | 2.00 |
| capric acid | 0.5 | % | 0.50 |
| lauric acid | 0.5 | % | 0.50 |
| triethanolamine | 350 | mM | 5.22 |
| tris(hydroxymethy)aminomethane | 350 | mM | 4.24 |
| sodium phosphate | 350 | mM | 4.20 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 1 | % | 2.00 |
| capric acid | 0.5 | % | 0.5 |
| lauric acid | 0.5 | % | 0.5 |
| citric acid | 350 | mM | 6.72 |
| tris(hydroxymethy)aminomethane | 350 | mM | 4.24 |
| triethanolamine | 350 | mM | 5.22 |
| sucralose | 0.2 | % | 0.20 |
| strawberry flavor | 0.4 | % | 0.4 |
| sodium hydroxide | pH adjust to 7.8 | — | — |
| water | q.s. | — | — |

| Component | Conc. | unit | % (w/v) |
|---|---|---|---|
| HIM2 | 2.5 | mg/ML | 0.25 |
| sodium cholate | 3 | % | 3.00 |
| oleic acid | 1 | % | 2.00 |
| capric acid | 0.5 | % | 0.50 |
| lauric acid | 0.5 | % | 0.50 |
| citric acid | 175 | mM | 3.36 |
| triethanolamine | 350 | mM | 5.22 |
| tris(hydroxymethy)aminomethane | 350 | mM | 4.24 |
| sodium phosphate | 175 | mM | 4.20 |
| sucralose | 0.2 | % | 0.20 |
| strawberry flavor | 0.4 | % | 0.4 |
| sodium hydroxide | pH adjust to 7.8 | — | — |
| water | q.s. | — | — |

While the above-described embodiments of pharmaceutical formulations comprise HIM2 as an active ingredient, it is to be understood that the active ingredient could be various other insulin drugs described herein. The active ingredient is preferably an insulin polypeptide-oligomer conjugate as described above.

The present invention will now be described with reference to the following examples. It should be appreciated that these examples are for the purposes of illustrating aspects of the present invention, and do not limit the scope of the invention as defined by the claims.

EXAMPLES

Example 1

Figure 1B:
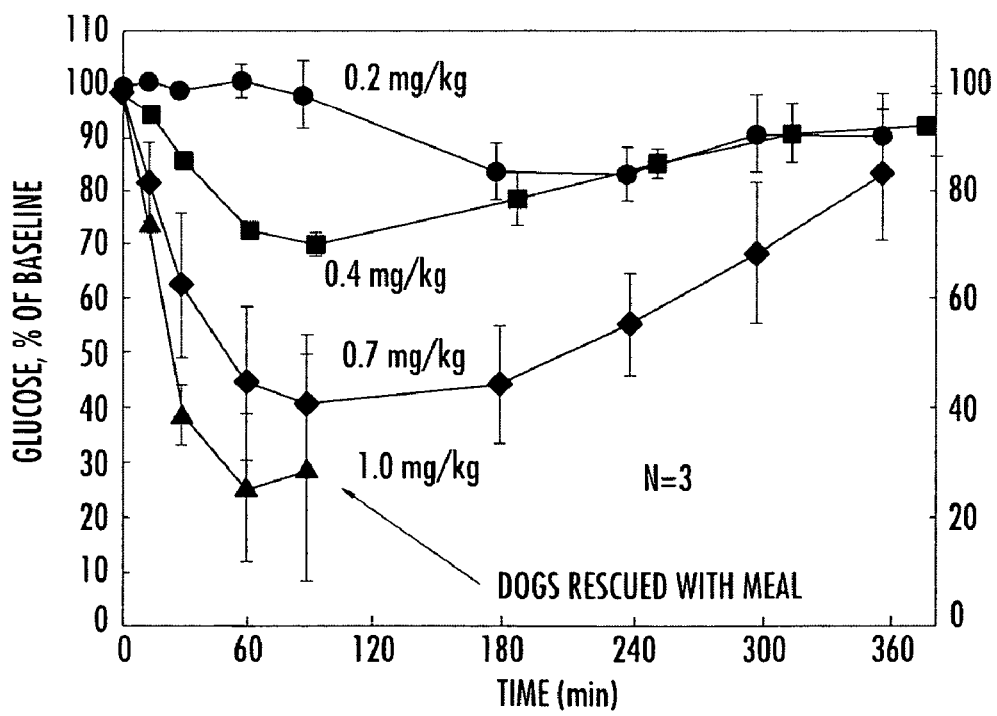
FIG. 1b shows glucose levels in pancreatectomized dogs receiving increasing doses of orally administered HIM2 according to embodiments of the present invention.

Numerous studies in both pancreactomized and normal, fasted dogs have shown that orally administered, conjugated insulin is rapidly absorbed in a dose-dependent manner and is associated with concomitant dose-dependent glucose-lowering effects. FIGS. 1a and 1b demonstrate these effects after various oral doses of HIM2 in pancreactomized dogs. At the highest dose of HIM2 studied, 1.0 mg/kg, all of the dogs required glucose rescue because of marked, symptomatic hypoglycemia.

Example 2

Figure 2:
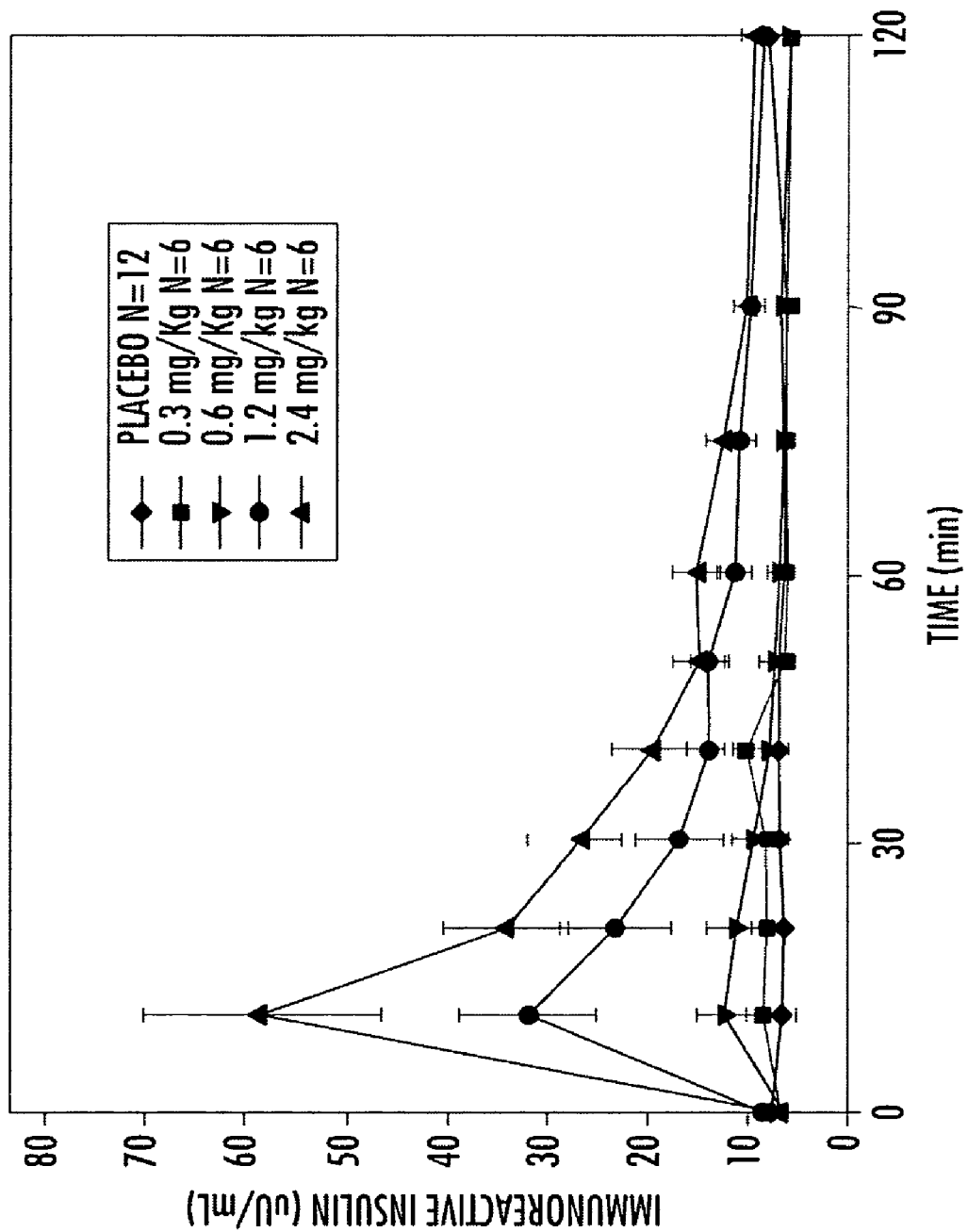
FIG. 2 shows serum insulin levels (+/−SEM) in normal volunteers after oral administration of HIMX at 4 ml dose volume according to embodiments of the present invention compared with oral administration of placebo.
Figure 3A:
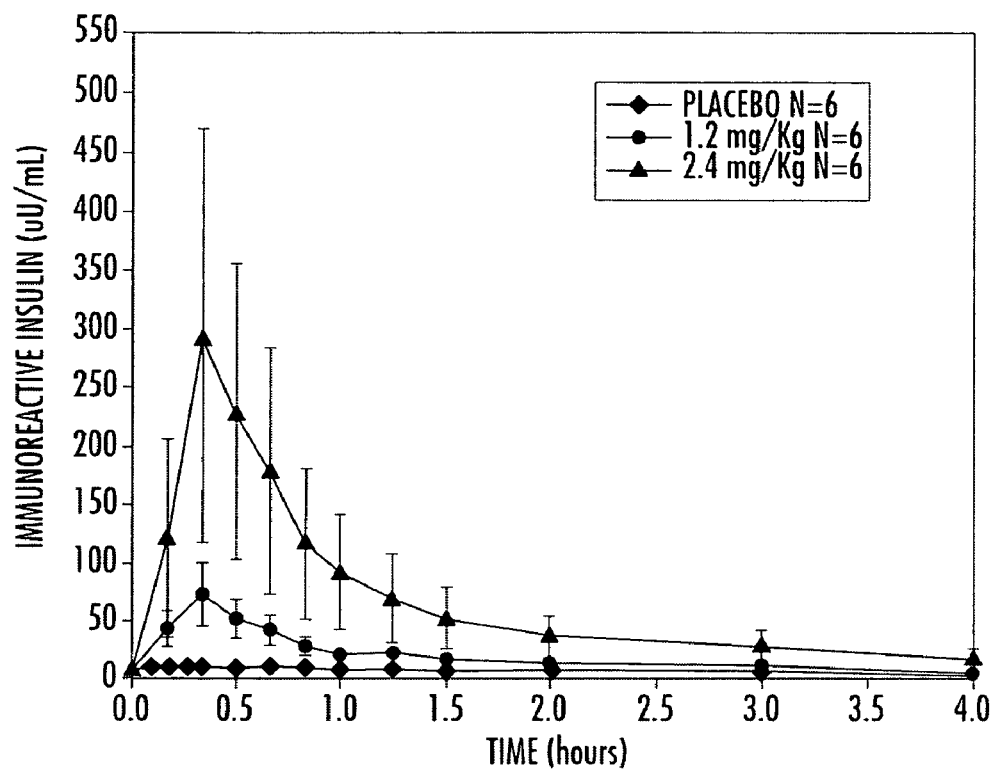
FIG. 3a shows serum insulin levels (+/−SEM) in normal volunteers after oral administration of HIMX at 20 ml dose volume according to embodiments of the present invention compared with oral administration of placebo.
Figure 3B:
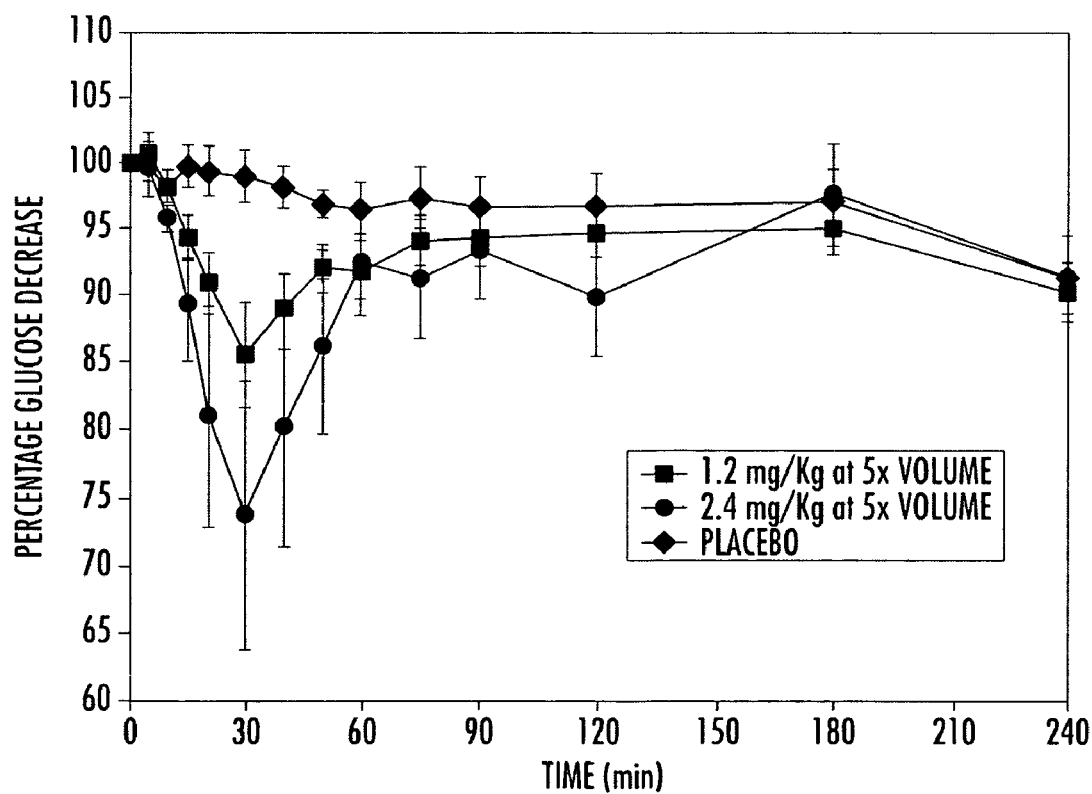
FIG. 3b shows serum glucose levels (+/−SEM) in normal volunteers after oral administration of HIMX at 4 ml dose volume according to embodiments of the present invention compared with oral administration of placebo.

A Phase I study in healthy volunteers was conducted. This study utilized an earlier, less purified (and, therefore, less active) form of conjugated insulin (hexyl insulin mixture, HIMX). HIMX is approximately five times less active than the more purified HIM2; therefore, a 2.4 mg/kg dose of HIMX is approximately equivalent to a 0.5 mg/kg does of HIM2. HIMX was administered in the fasting state at four different dose levels, after which peripheral insulin and glucose concentrations were measured. As shown in FIG. 2, insulin concentrations reached peak levels ($C_{max}$) in the physiological range at 10-15 minutes after oral dosing of HIMX (4 ml dose volume) and were dose dependent. When a larger dosing volume (20 ml) was utilized for the same doses, the resulting insulin $C_{max}$ at all doses was significantly higher, demonstrating a marked influence of formulation volume on absorption (FIG. 3a). FIG. 3b shows the plasma glucose values seen after the 20 ml dose volume, confirming the dose-dependent, glucose lowering effects of conjugated insulin seen previously in dogs. No adverse effects of HIMX were noted in this study of healthy volunteers.

Example 3

The objectives of this study in Type 1 diabetic patients were to: 1) determine the safety and tolerance of escalating doses of orally administered HIM2; 2) estimate the kinetics of HIM2 after oral dosing compared with subcutaneous dosing with regular insulin and placebo; and 3) evaluate the pharmacodynamics of HIM2 compared with subcutaneous insulin using blood glucose as the marker of drug effect.

This was a randomized, double-blind, three-dose plus active (subcutaneous insulin) control, double-dummy, placebo-controlled, five-period, cross-over study. After an overnight fast during which euglycemia was maintained by intravenous insulin administration, the insulin was then discontinued, and, after a 2 hour washout period, single doses of oral placebo or HIM2 (0.15, 0.3, and 0.6 mg/kg), and subcutaneous regular insulin (4 IU) or insulin placebo, were administered to patients in a randomized fashion as shown in Table 1 below. Plasma glucose and insulin levels were then measured serially over the following four hours.

TABLE 1

| | Route of Administration and Treatment | | | | | |
|---|---|---|---|---|---|---|
| | Oral | | | | Subcutaneous | |
| | | | | | | Human |
| Study Period | Placebo | 0.15 mg/kg HIM2 | 0.3 mg/kg HIM2 | 0.6 mg/kg HIM2 | Placebo | Recombinant Insulin (4 IU) |
| 1 | P1, P2 | | P3, P4, P5, P6, P7, P8 | | P3, P4, P5, P6, P7, P8 | P1, P2 |
| 2 | P3, P4 | | P1, P2 | P5, P6, P7, P8 | P1, P2, P5, P6, P7, P8 | P3, P4 |
| 3 | P5, P6 | P7, P8 | | P1, P2, P3, P4 | P1, P2, P3, P4, P7, P8 | P5, P6 |
| 4 | P7, P8 | P1, P2, P3, P4, P5, P6 | | | P1, P2, P3, P4, P5, P6 | P7, P8 |
| 5 | P1, P2, P3, P4, P5, P6, P7, P8 | | | | P1, P2, P3, P4, P5, P6, P7, P8 | |

Figure 4A:
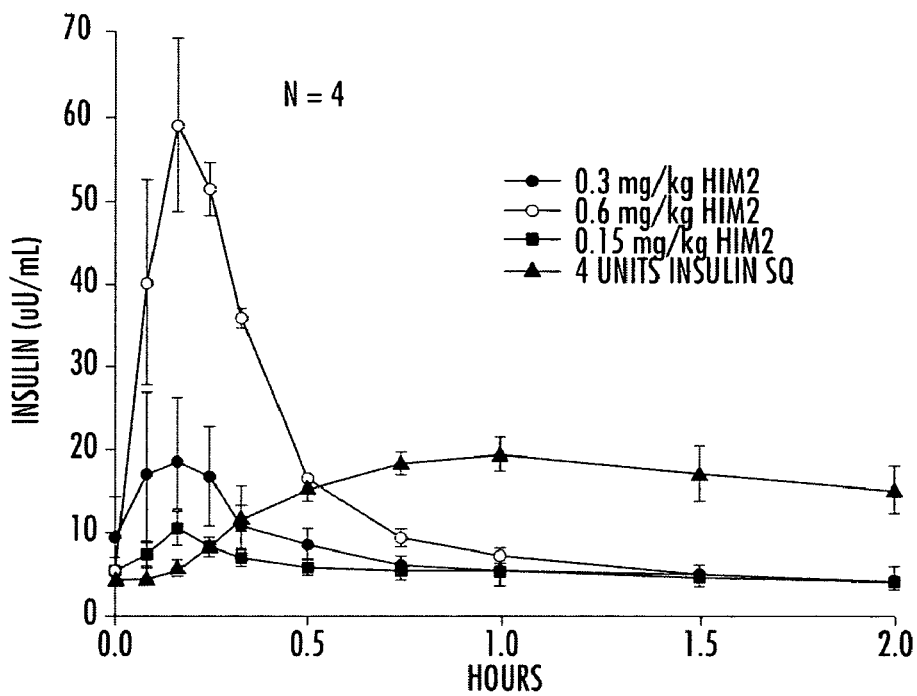
FIG. 4a shows peripheral insulin concentrations after oral administration of HIM2 in Type 1 diabetic patients according to embodiments of the present invention compared with subcutaneous (SQ) administration of 4 Units of insulin.
Figure 4B:
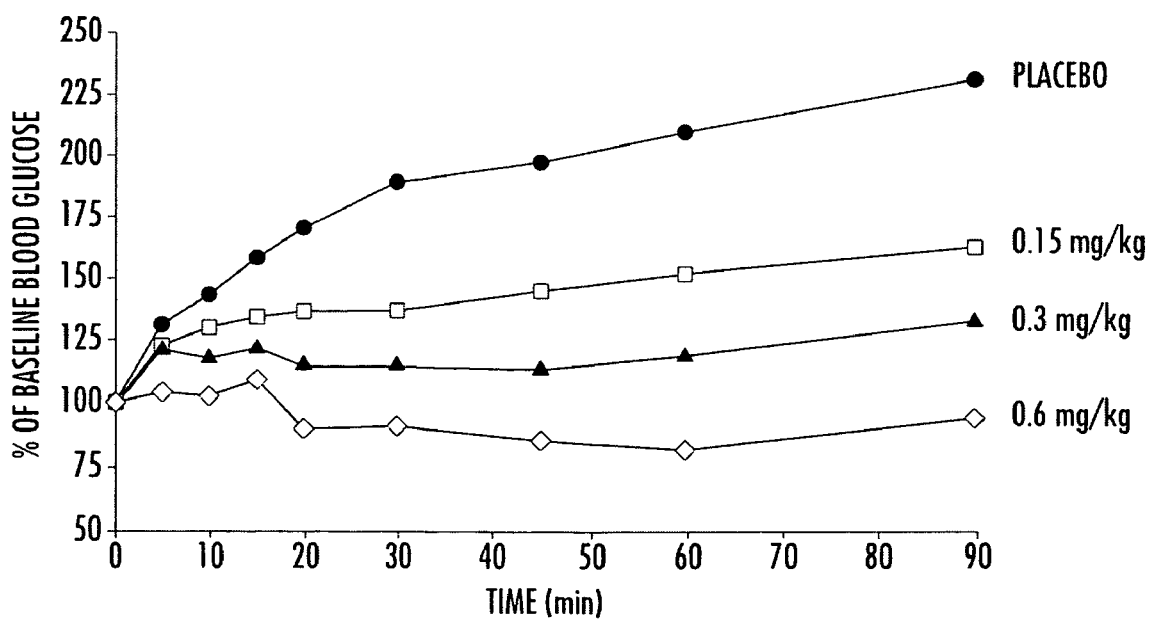
FIG. 4b shows peripheral glucose concentrations after oral administration of HIM2 in Type 1 diabetic patients according to embodiments of the present invention compared with oral administration of placebo.

HIM2 was well tolerated and there was no evidence of a dose-related increase in adverse events. No patient became symptomatically hypoglycemic. After oral administration of HIM2, mean plasma insulin levels increased in a dose-related manner and peaked within 15 minutes of dosing, returning to baseline within 20 minutes (FIG. 4a). At the 0.6 mg/kg dose, insulin levels increased markedly in 7 of 8 (88%) of patients. By comparison, 4 IU of regular insulin administered subcutaneously produced a broad insulin peak that did not reach an average maximum concentration ($C_{max}$) value until 66 minutes after injection. In this group of patients, HIM2 appeared to prevent or attenuate the significant rise in plasma glucose that is seen in diabetic patients when all insulin therapy is removed (FIG. 4b). Additionally, a dose-dependent glucose-stabilizing effect was seen in these patients, reflecting an apparent decrease in hepatic glucose production after HIM2 dosing (FIG. 4b). The duration of the glucose effects lasted up to 120 minutes, which was significantly longer than predicted from the duration of the plasma insulin increases.

Single doses of HIM2 at 0.15, 0.3, and 0.6 mg/kg were well tolerated in Type 1 diabetic patients and there was no evidence of a dose-related increase in adverse events. Dose-related increases in plasma insulin levels occurred, with rapid attainment of $C_{max}$ values within 15 minutes and a return to baseline values within 90-120 minutes. The expected increase in plasma glucose levels after withdrawal of any other insulin treatment was attenuated or prevented and the effects on glucose persisted substantially longer than predicted from the duration of plasma insulin increases. These results indicated that orally administered HIM2 likely influences peripheral glucose levels by a combination of decrease liver glucose output and peripheral insulin-like activity. A potential role for HIM2 in management of diabetes by reproduction of physiological portal-hepatic delivery is suggested.

Example 4

A second early Phase II study utilized a 2-sequential-dose, escalation scheme in Type 1 diabetic patients. As in the first Type 1 diabetic study, the patients were fasted overnight and maintained in a euglycemic state by intravenous insulin administration. In the morning, after discontinuation of intravenous insulin and a 2-hour washout period, the patients were given 0.6, 0.8, or 1.0 mg/kg doses of HIM2 in groups of six patients at each dose level. Measurements of peripheral glucose and insulin were obtained at regular intervals after dosing. A second dose of HIM2 was administered 2 hours after the first dose in order to assess the effects of a "priming" dose of oral HIM2 on hepatic glucose production and peripheral insulin concentrations. The liquid formulation used in this study was found to be irritating to the oropharynx in the first six subjects that received the drug. Therefore, the study was interrupted while a replacement capsule formulation was developed. A semi-solid dosage form in two capsule sizes was used in the re-started study.

| 3 mg HIM2 capsule formulation: | | | | |
|---|---|---|---|---|
| Component | MS Number | mg/ capsule | percentage | weight |
| HIM2 as protein | 236 | 3.00 | 1.6 | 4.35 |
| Polyethylene Glycol 400 | 027 | 30.00 | 16.2 | 43.5 |
| Water USP | 012 | 1.5 | 0.8 | 2.18 |
| Labrasol | 240 | 117.00 | 63.2 | 169.65 |
| Syloid 244 | 238 | 33.00 | 17.8 | 47.85 |
| Sodium Phosphate Monobasic | 239 | 0.09 | 0.05 | 0.13 |
| Sodium Phosphate Dibasic | 237 | 0.41 | 0.23 | 0.59 |
| Total | | 185 | 100 | 268.25 |

Size "3" Green Gelatin Capsules

| 15 mg HIM2 capsule formulation: | | | | |
|---|---|---|---|---|
| Component | MS Number | mg/ capsule | percentage | weight |
| HIM2 as protein | 236 | 15.00 | 3.2 | 10.2 |
| Polyethylene Glycol 400 | 027 | 75.0 | 16.0 | 51.00 |
| Water USP | 012 | 3.8 | 0.8 | 2.58 |
| Labrasol | 240 | 292.0 | 62.1 | 198.56 |
| Syloid 244 | 238 | 83.0 | 17.6 | 56.44 |
| Sodium Phosphate Monobasic | 239 | 0.2 | 0.04 | 0.14 |
| Sodium Phosphate Dibasic | 237 | 1.0 | 0.21 | 0.68 |
| Total | | 470 | 100 | 319.60 |

Size: "O EL" Green Gelatin Capsules

Figure 5:
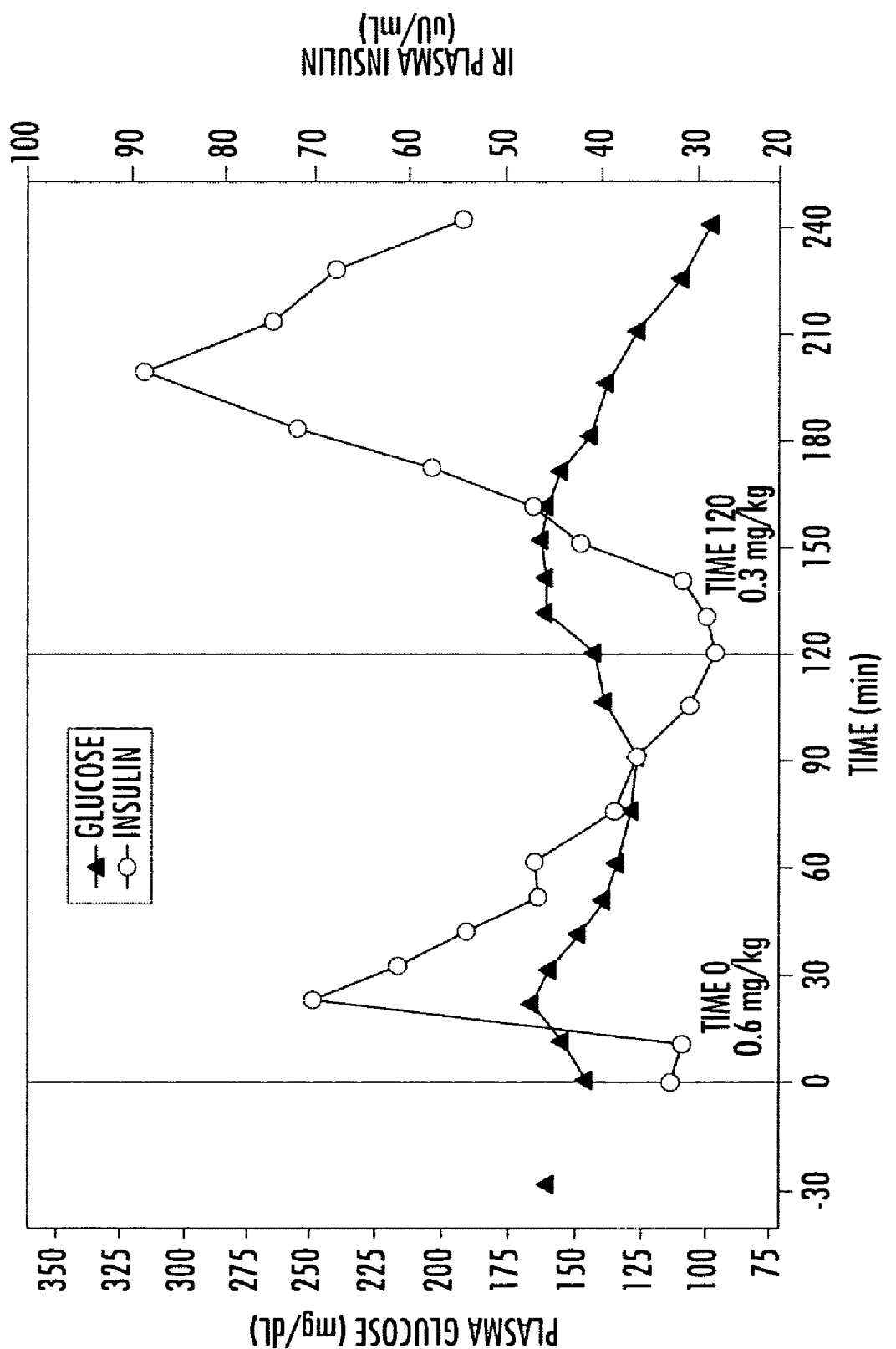
FIG. 5 shows effects of two sequential doses of HIM2 orally administered according to embodiments of the present invention on glucose and insulin in a fasted Type 1 diabetic patient who has no other insulin provided.
Figure 6:
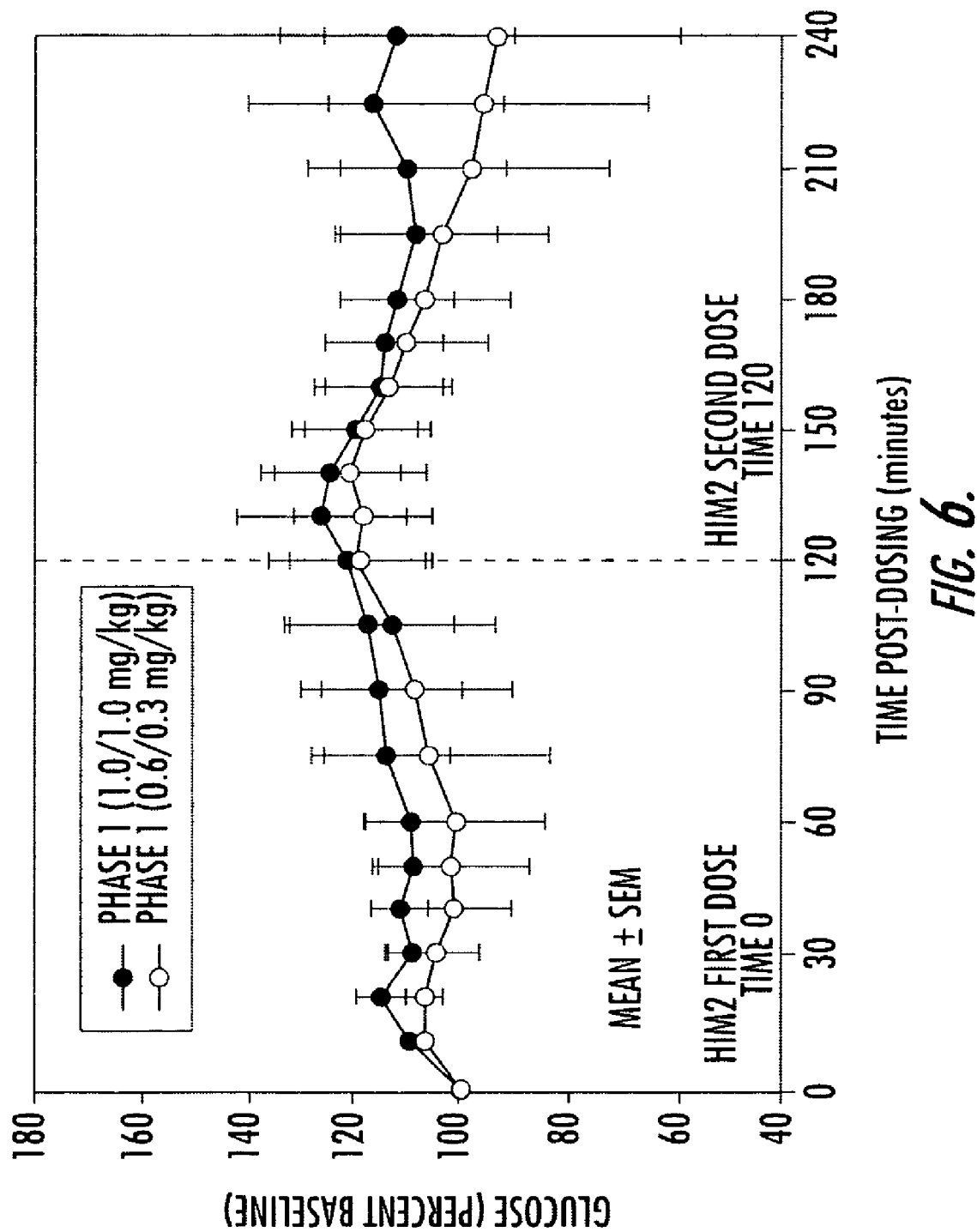
FIG. 6 shows effects of two sequential doses of HIM2 orally administered according to embodiments of the present invention on plasma glucose in fasted type 1 diabetic patients.

Results from this study demonstrate that (a) the new capsule formulation is well-tolerated, (b) no side effects were seen, and (c) effects on blood glucose varied from stabilization to moderate decreases from baseline values over one to two hours after administration (FIG. 5). There was not a significant difference in the magnitude of the glucose responses across the dose range used, as seen in FIG. 6, which shows the mean responses at the lowest and highest doses used in the study. No hypoglycemia was experienced by the patients at any dose. These results suggest that oral HIM2, at the doses used, influences glucose primarily by affecting hepatic glucose output and without significant peripheral insulin effects.

Example 5

Figure 7:
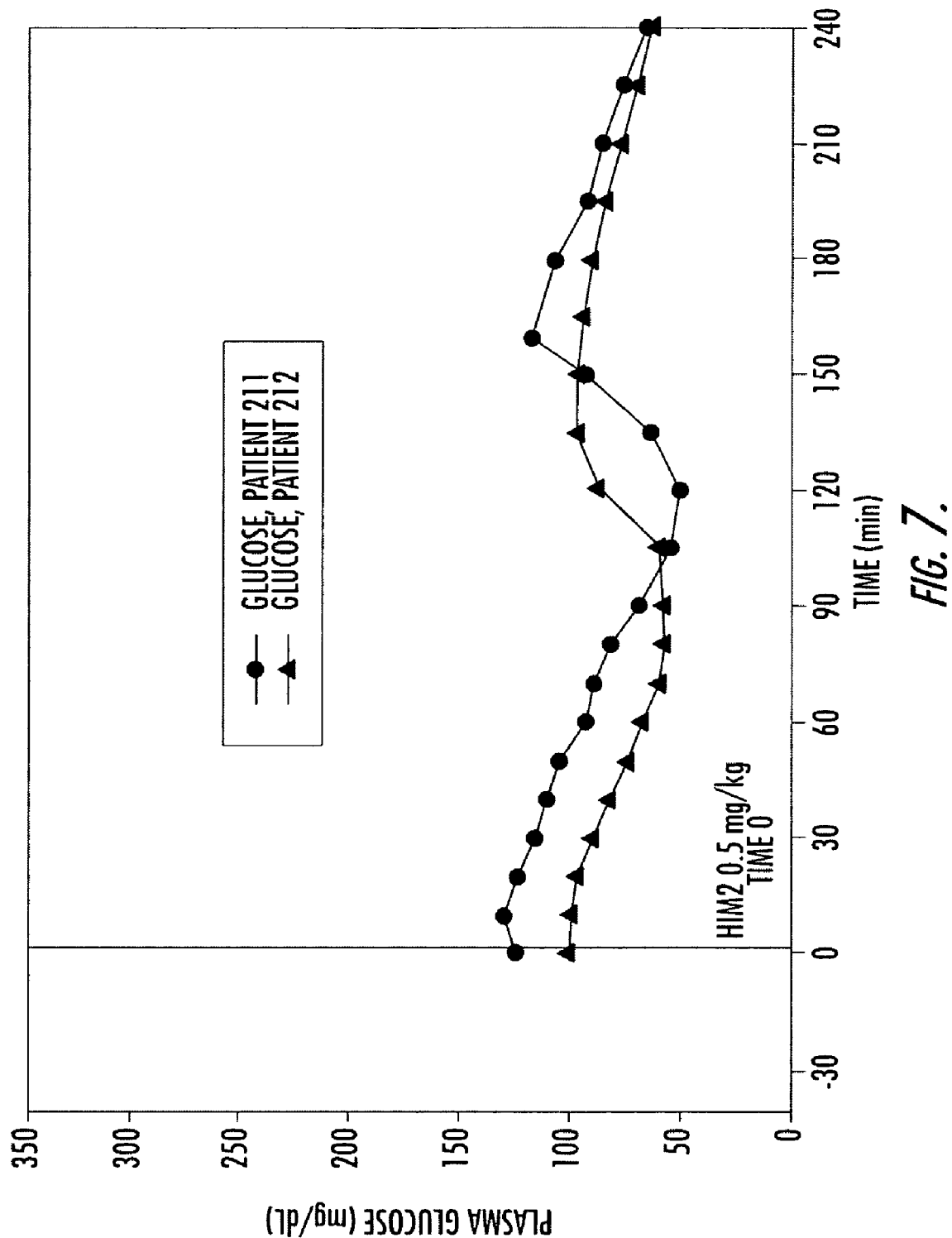
FIG. 7 shows effects on plasma glucose in fasting Type 1 diabetic patients after oral administration of HIM2 according to embodiments of the present invention.
Figure 8:
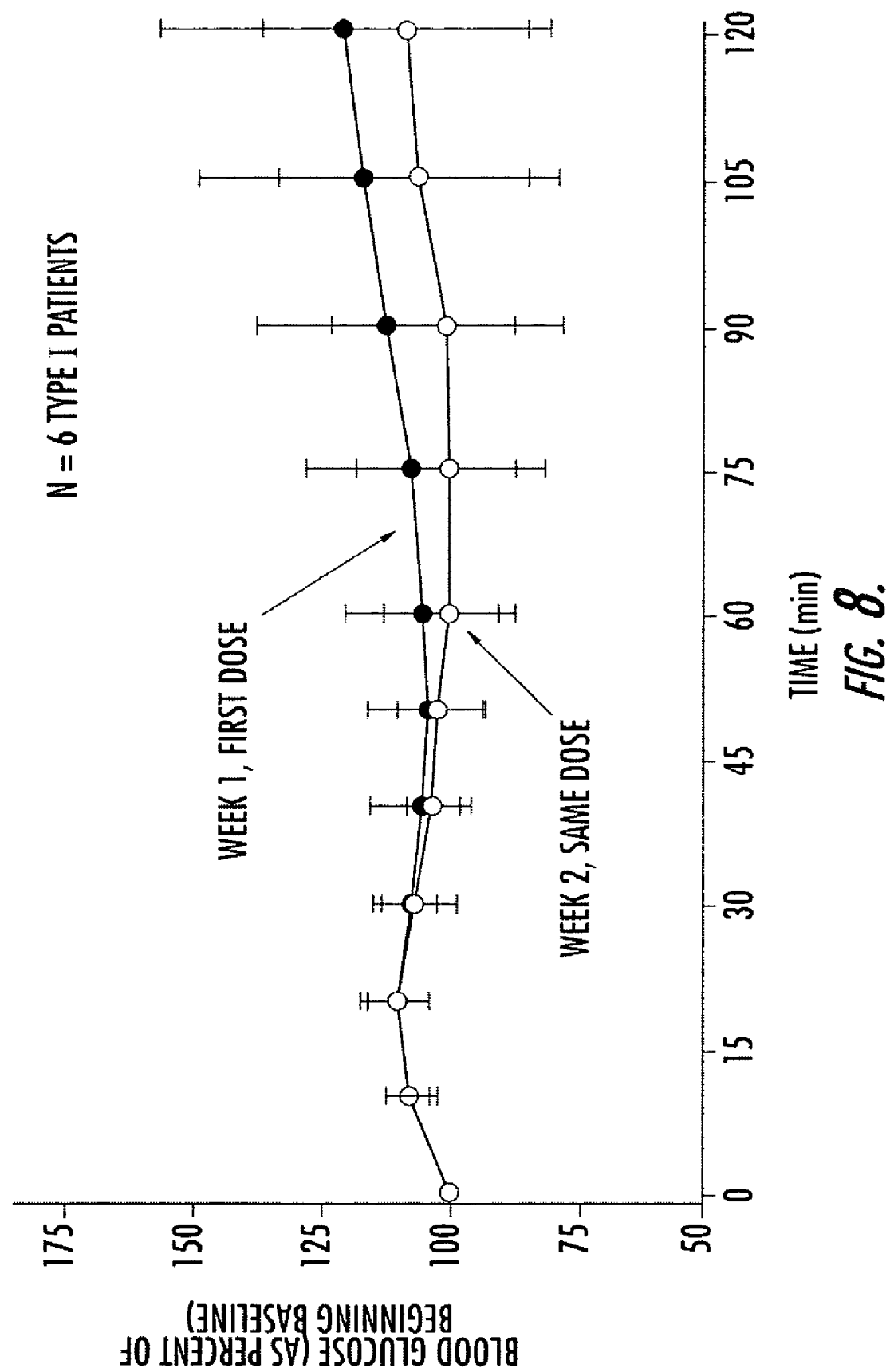
FIG. 8 shows blood glucose effects in Type 1 patients after oral administration of HIM2 according to embodiments of the present invention, where oral administration of the same dose of HIM2 was repeated one week later.
Figure 9:
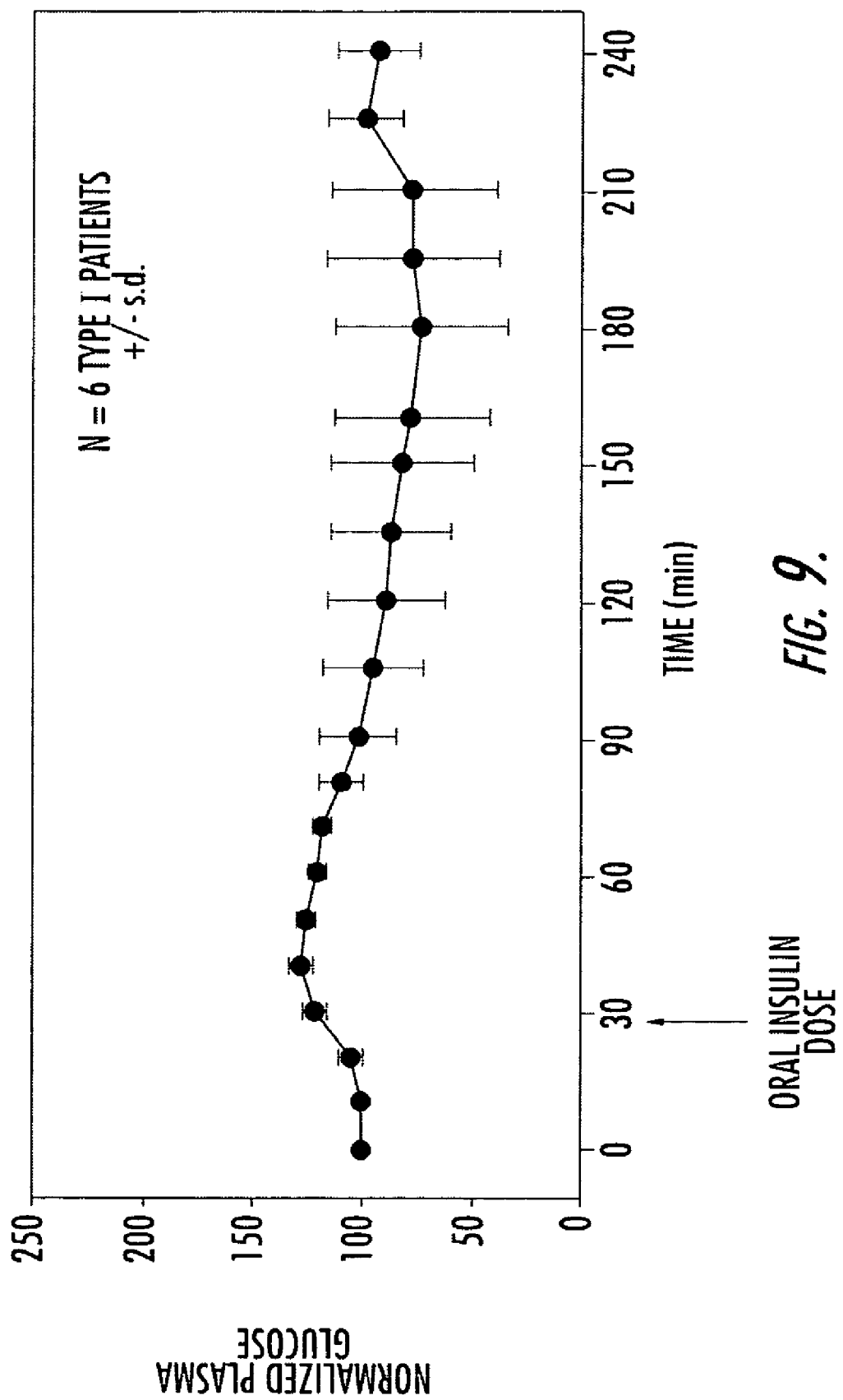
FIG. 9 shows effects on fasting blood glucose in Type 1 patients after oral administration of HIM2 with co-administration of basal (pump) insulin according to embodiments of the present invention.
Figure 10:
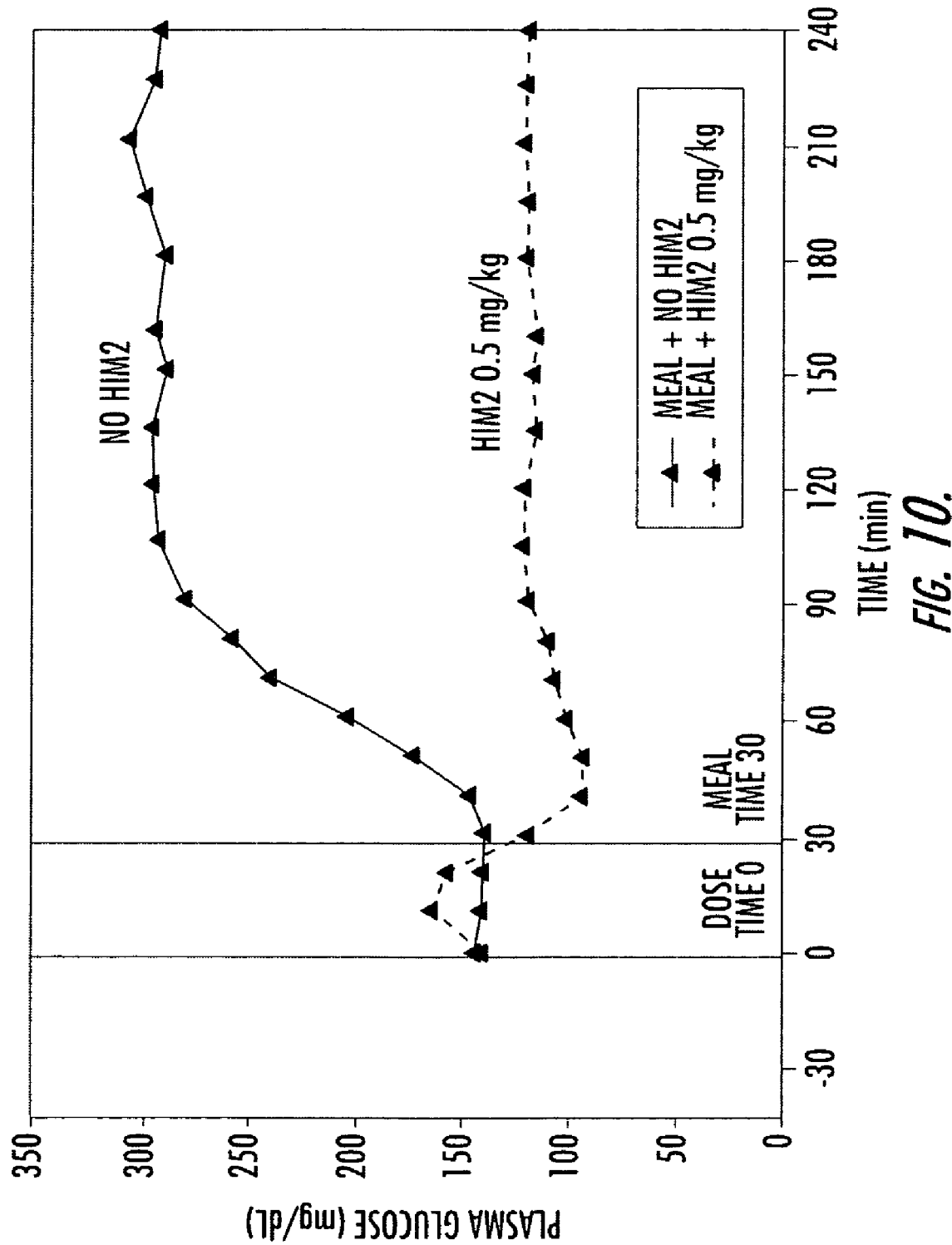
FIG. 10 shows effects on post-prandial glucose in a Type 1 diabetic patient after oral administration of HIM2 according to embodiments of the present invention.
Figure 11:
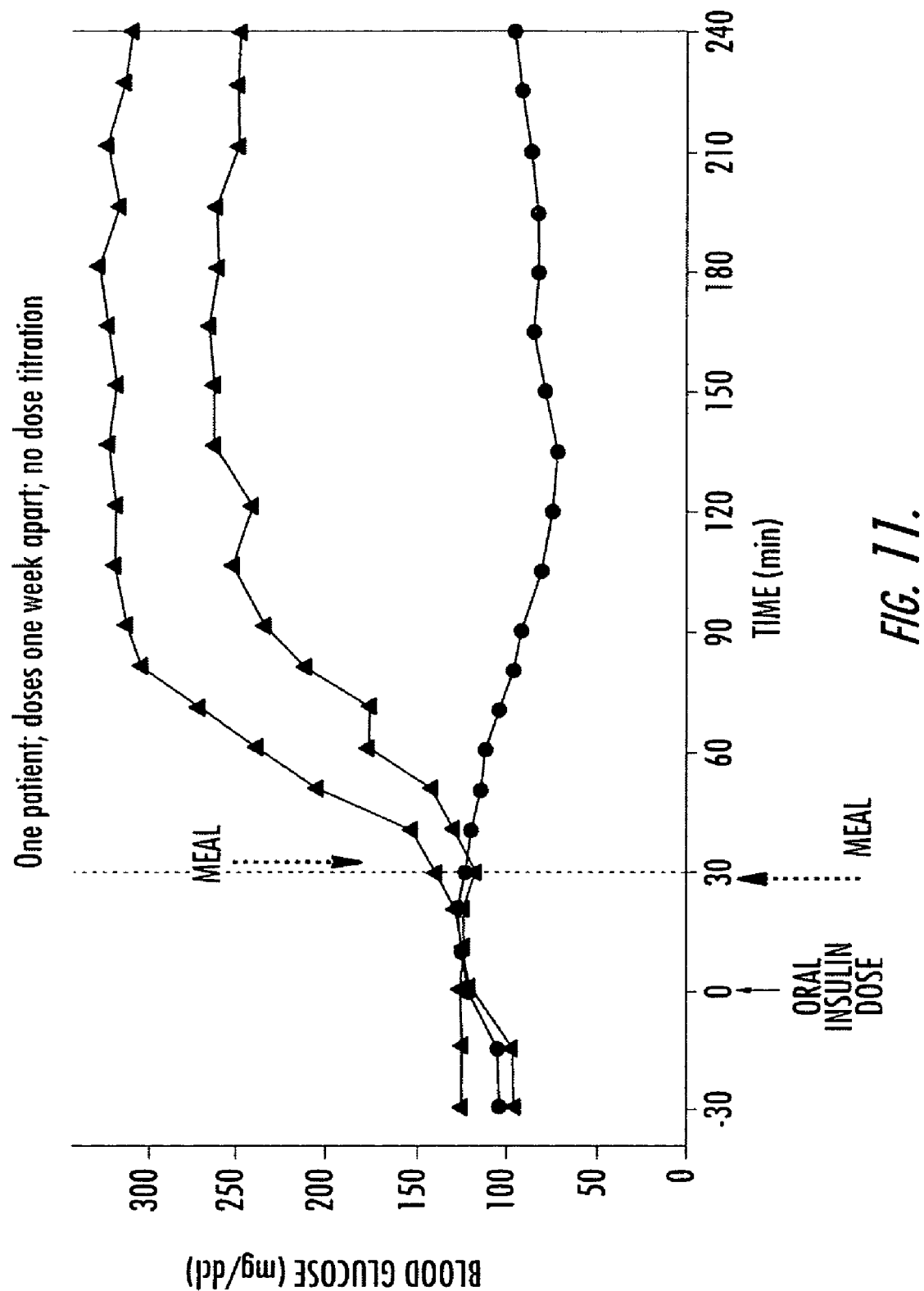
FIG. 11 shows effects on post-prandial glucose in Type 1 diabetic patients after oral administration of HIM2 according to embodiments of the present invention.
Figure 12:
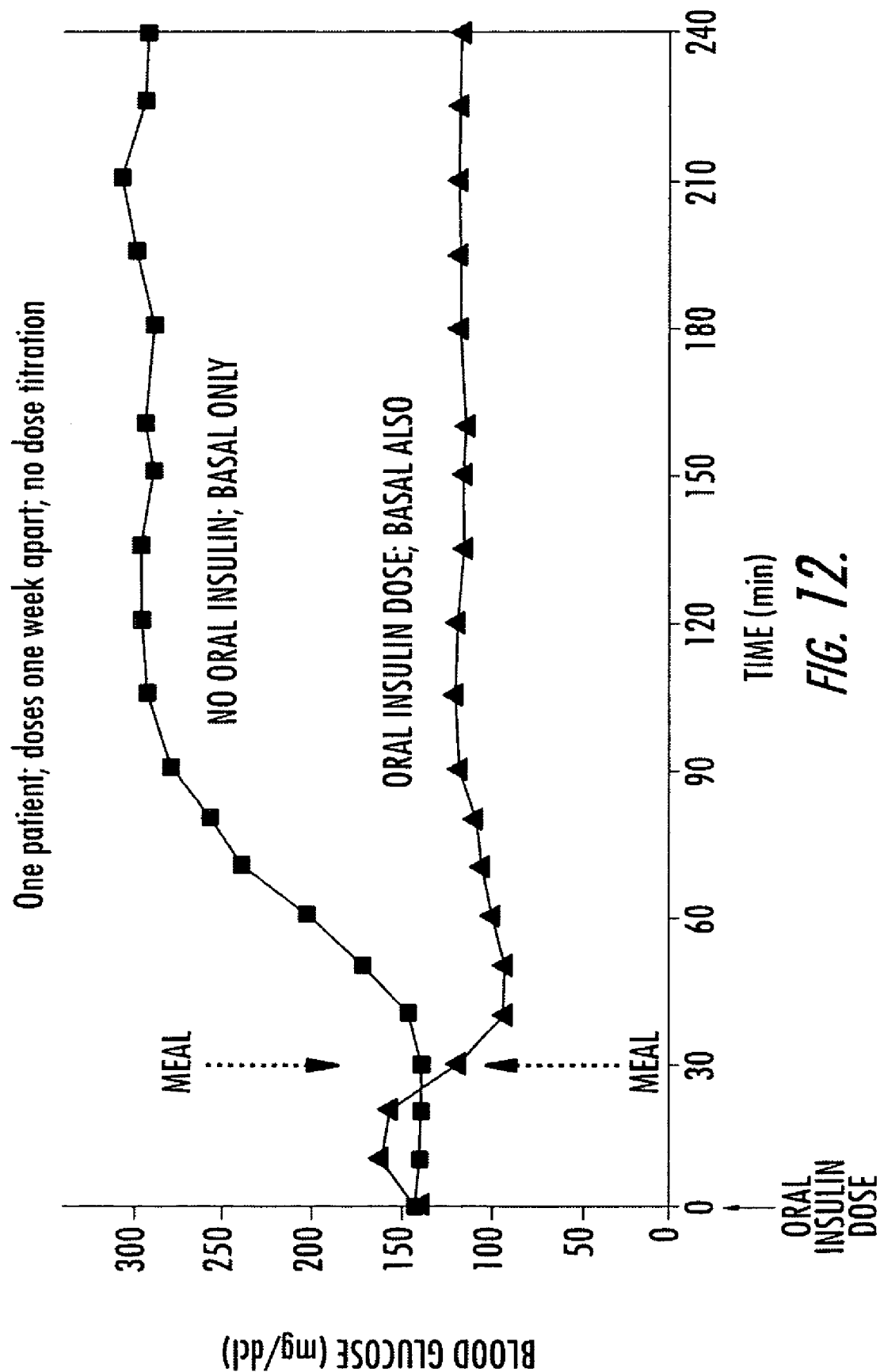
FIG. 12 shows effects on post-prandial glucose in Type 1 diabetic patients after oral administration of HIM2 according to embodiments of the present invention.
Figure 13:
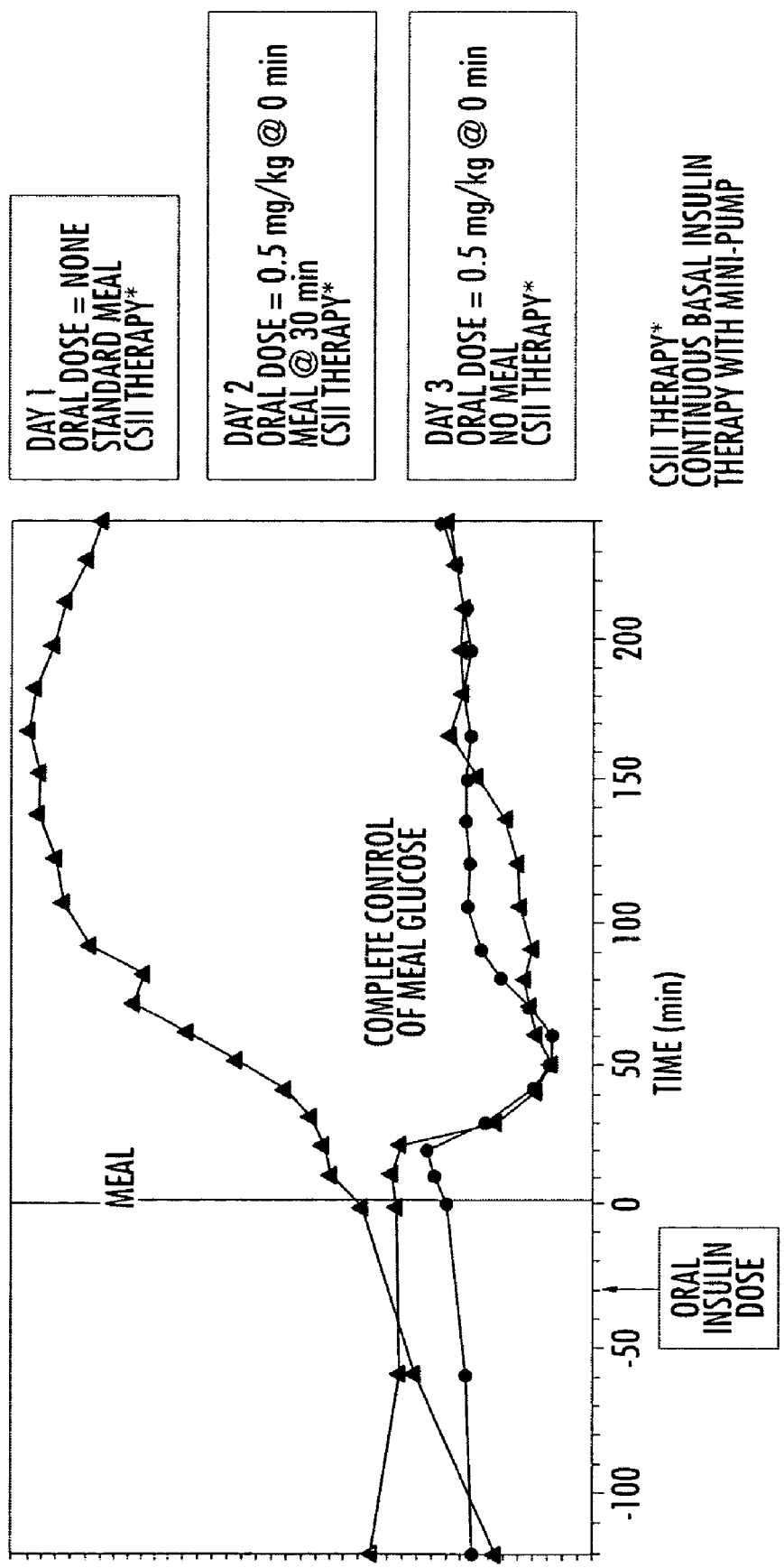
FIG. 13 shows effects on post-prandial glucose in Type 1 diabetic patients after oral administration of HIM2 according to embodiments of the present invention.

Two additional studies in Type 1 diabetic patients using the capsule formulation have explored the influence of food on absorption and glucose-lowering activity of HIM2 as well as HIM2 effects when administered concomitantly with a standard basal regimen (provided by continuous subcutaneous insulin infusion or CSII). Preliminary results of the first study indicate that a standard meal ingested at the same time as HIM2 dosing may result in attenuation of HIM2 absorption and glucose lowering effects. However, if HIM2 is administered 30 minutes prior to ingestion of a standard meal, absorption and effects on glucose are substantially preserved. The second study evaluates the absorption and effects of HIM2 when dosed in fasted Type 1 patients that are maintained on basal insulin by CSII, followed by either continued fast or a standard meal. Preliminary results in a limited number of patients indicate that HIM2 not only reduces fasting glucose but also attenuates or prevents expected post-prandial increases in plasma glucose concentrations (FIGS. 7 and 8). A first study in Type 2 diabetic patients has demonstrated similar effects of HIM2 on fasting blood glucose levels in a limited number of patients. Other studies are investigating the potential for HIM2 to attenuate post-prandial hyperglycemia in Type 2 diabetic patients. In one study involving 12 Type 2 patients, a single oral dose (without titration) is followed by a meal. In another study involving 24 Type 2 patients, 3 doses/day (without titration) with meals are given for 3 days. Also, a late night dose is given to see possible effects on hyperglycemia.

Example 6

Male, CF-1 mice (n=5-10 per group) were fasted overnight, then administered either HIM2 (1.25 or 2.5 mg/kg, p.o., in a formulation shown in the table below, 10 mL/kg) or recombinant human insulin (12.5 or 25 μg/kg, abdominal sc, in 1% acetate buffer, pH 4.1).

| Component | Conc. | unit | % (w/v) |
| --- | --- | --- | --- |
| HIM2 | 2.5 | mg/ML | 0.25 |
| sodium cholate | 3 | % | 3.00 |
| oleic acid | 1 | % | 2.00 |
| capric acid | 0.5 | % | 0.5 |
| lauric acid | 0.5 | % | 0.5 |
| citric acid | 350 | mM | 6.72 |
| tris(hydroxymethy)aminomethane | 350 | mM | 4.24 |
| triethanolamine | 350 | mM | 5.22 |
| sucralose | 0.2 | % | 0.20 |
| strawberry flavor | 0.4 | % | 0.4 |
| sodium hydroxide | pH adjust to 7.8 | — | — |
| water | q.s. | — | — |

After 15, 20 or 60 minutes, blood samples were obtained in heparinized syringes, under ether anesthesia, from both the portal vein (PV) and vena cava (VC) of each animal. A drop of blood was spotted onto a glucometer for measurement of blood glucose. The remaining sample was centrifuged to separate plasma for determination of immunoreactive insulin by ELISA (ALPCO).

Figure 16:
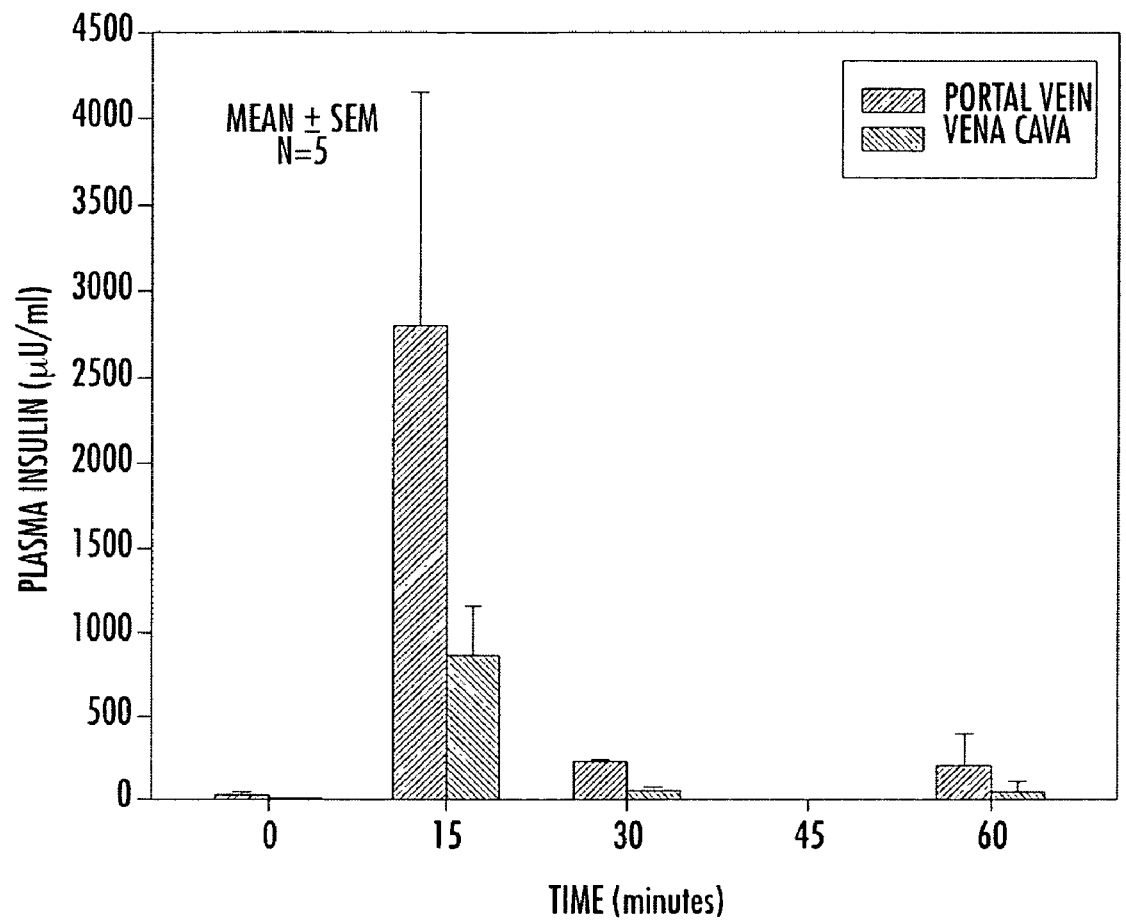
FIG. 16 shows portal vein (PV) and vena cava (VC) plasma insulin levels after oral administration of HIM2 at 2.5 mg/kg according to embodiments of the present invention.
Figure 17A:
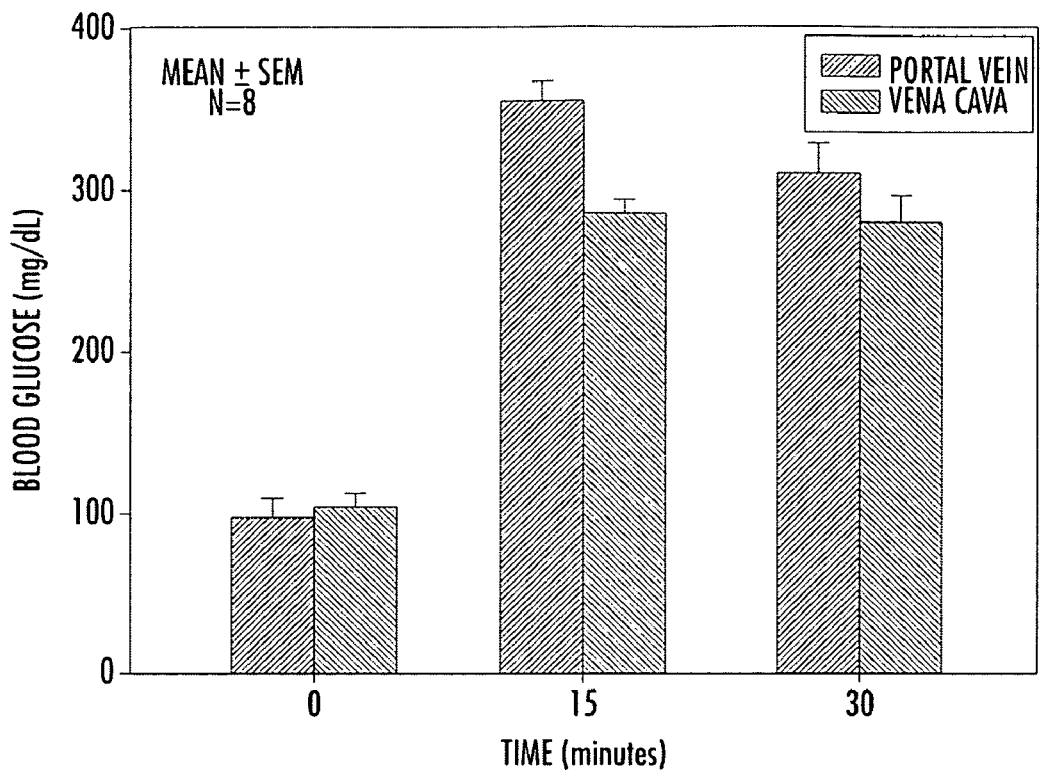
FIG. 17 shows portal vein (PV) and vena cava (VC) blood glucose and plasma insulin levels after oral administration of dextrose solution in fasted mice for purposes of comparison.
Figure 17B:
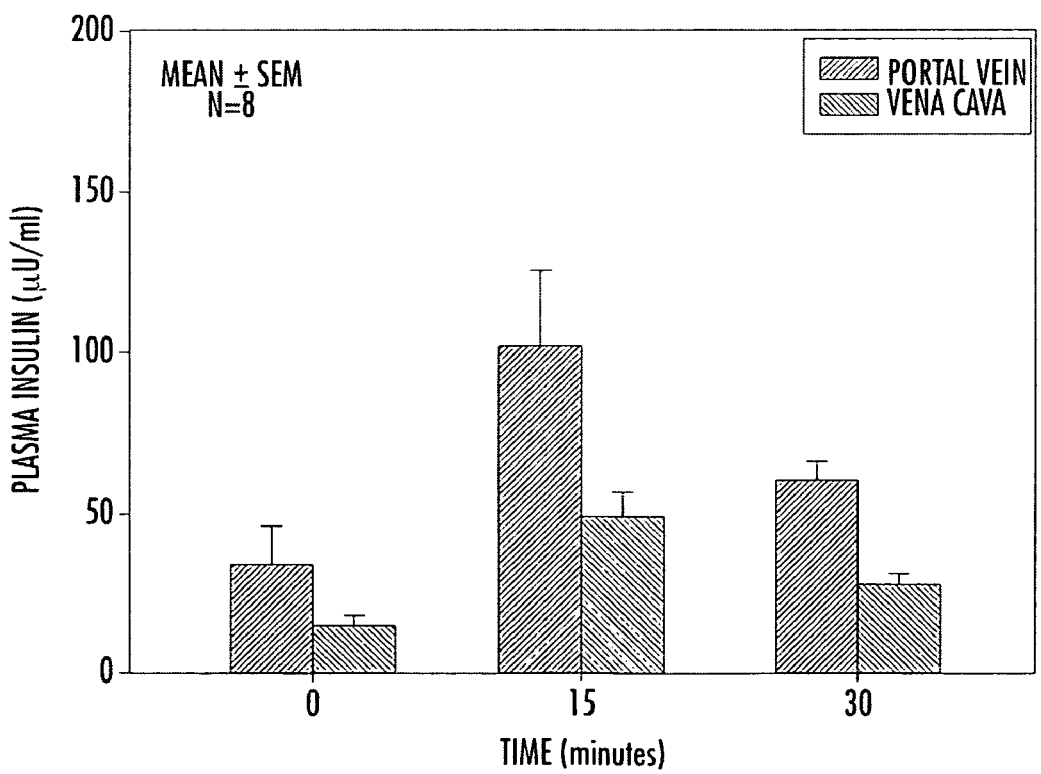

As illustrated in FIG. 16, large increases of insulin (up to 2789 μU/mL) were seen in the PV by 15 minutes after oral administration of HIM2, and insulin concentration fell to 221 μU/mL by 30 minutes after administration. This profile resembles that of first phase insulin secretion in response to a meal as illustrated in FIG. 17, which shows portal vein and vena cava blood glucose and plasma insulin levels after oral administration of dextrose solution in fasted mice. As further illustrated in FIG. 16, peak insulin levels in the VC were 31 to 36% of those in the PV.

Figure 18:
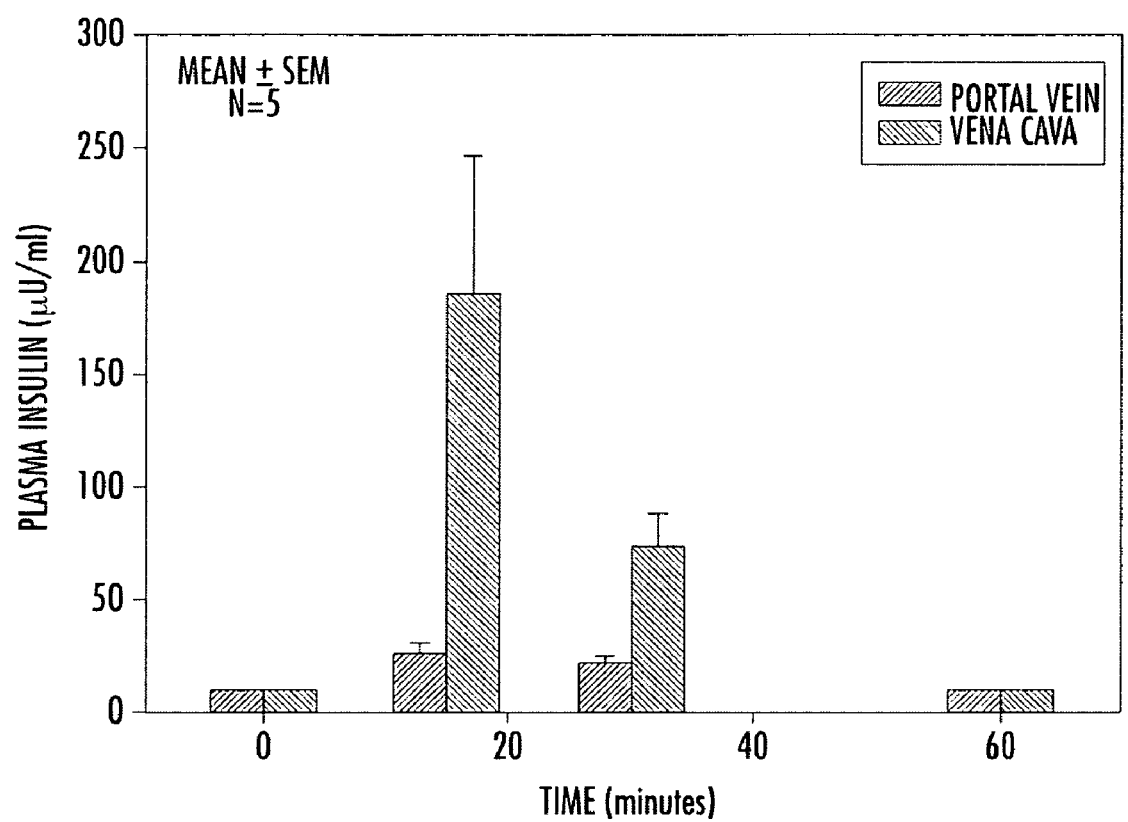
FIG. 18 shows portal vein (PV) and vena cava (VC) plasma insulin levels after subcutaneous administration of human recombinant insulin at 25 μg/kg for purposes of comparison.

In contrast, as illustrated in FIG. 18, subcutaneous administration of insulin produced 2.4-6.9 times higher concentrations in the VC (i.e., periphery) (up to 186 μU/mL, 15 minutes after administration) than in the PV. There was also a slower return to baseline (74 μU/mL, 30 minutes after administration).

Figure 19:
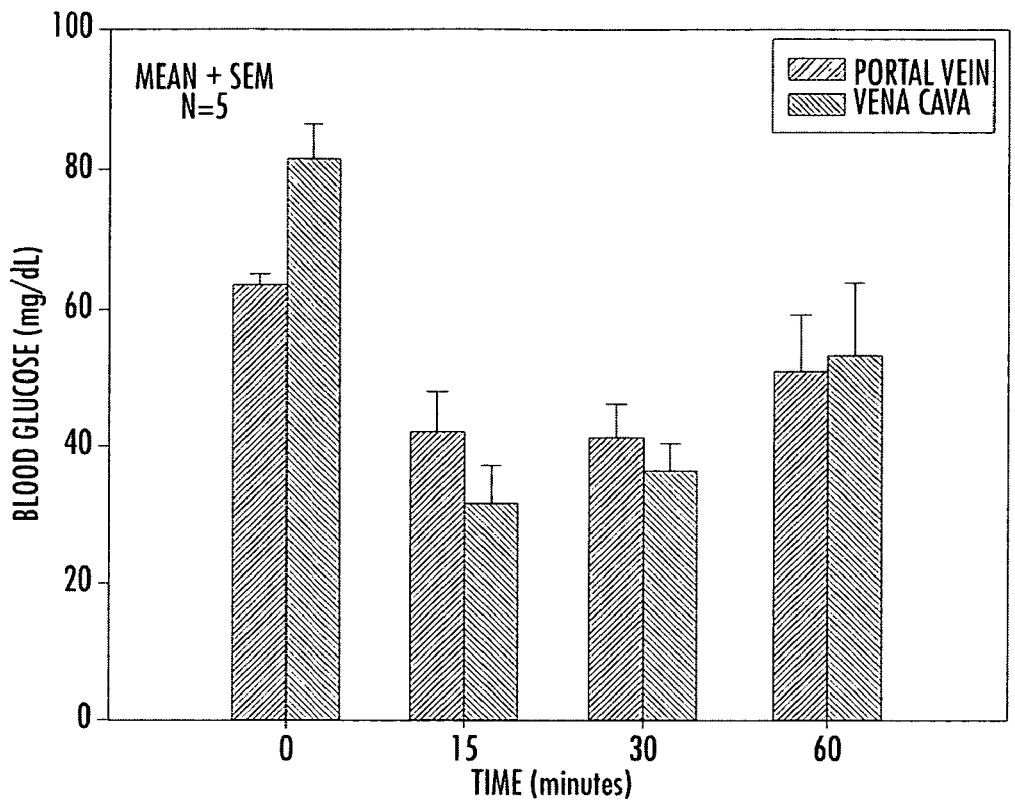
FIG. 19 shows vein (PV) and vena cava (VC) plasma glucose levels after oral administration of HIM2 at 2.5 mg/kg ($2\times ED_{50}$) according to embodiments of the present invention.
Figure 20:
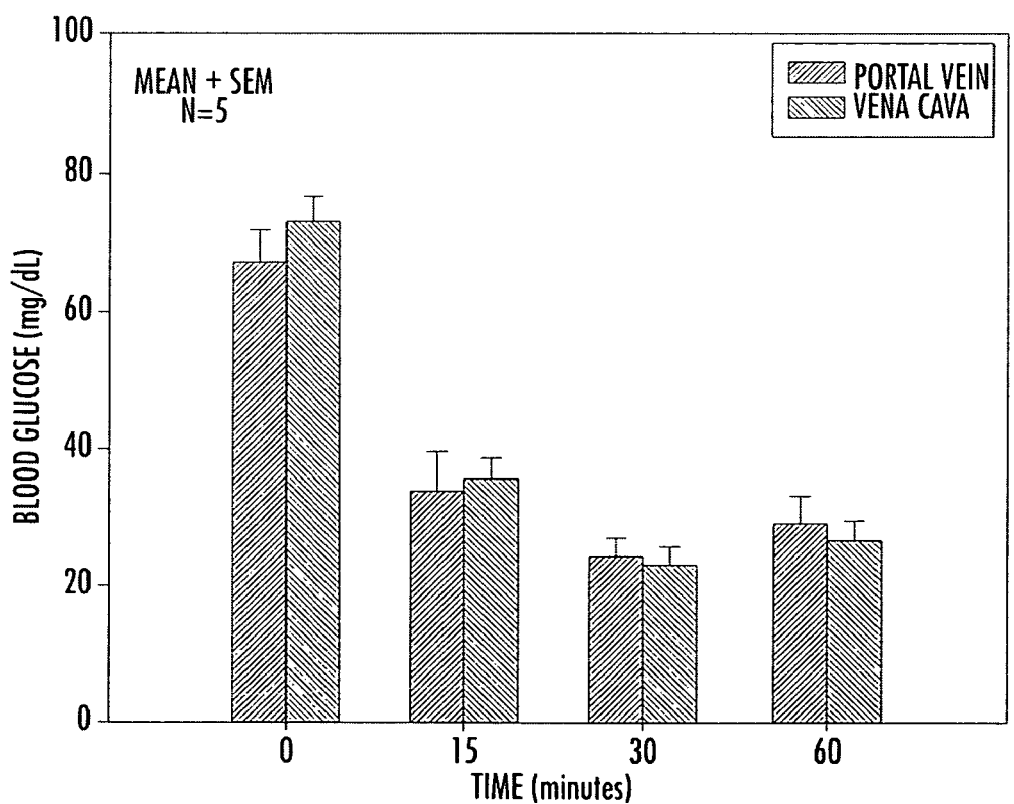
FIG. 20 shows vein (PV) and vena cava (VC) plasma glucose levels after subcutaneous administration of human recombinant insulin at 25 μg/kg ($2\times ED_{50}$) for the purposes of comparison.

Despite the marked differences in insulin levels, HIM2 did not produce correspondingly greater falls in blood glucose, when compared to the falls in blood glucose produced by subcutaneous administration of insulin, in these non-diabetic mice. For example, as illustrated in FIG. 18, oral administration of HIM2 caused a blood glucose drop to approximately 31 mg/dL in the VC compared to a blood glucose drop to about 23 mg/dL in the VC illustrated in FIG. 19 for subcutaneous administration of insulin. These results appear to indicate that oral administration of HIM2 has fewer tendencies to induce hypoglycemia than subcutaneous administration of insulin.

In untreated mice, blood glucose was higher in the VC than in the PV. This PV-VC difference was reversed by oral administration of HIM2, but was not reversed by subcutaneous administration of insulin. These results appear to indicate that oral administration of HIM2 provides a greater suppression of hepatic glucose output than subcutaneous administration of insulin.

In the specification, there has been disclosed typical preferred embodiments of the invention and, although specific terms are employed, they are used in a generic and descriptive sense only and not for purposes of limitation, the scope of the invention being set forth in the following claims.

What is claimed is:

1. A composition consisting essentially of substantially monodispersed insulin polypeptide-oligomer conjugates having the structure of Formula V

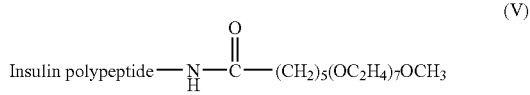

(V)

wherein the substantially monodispersed insulin polypeptide-oligomer conjugates comprise an insulin polypeptide and an oligomer and wherein the oligomer is coupled to a lysine at the B29 position of the insulin polypeptide.

2. The composition of claim 1, wherein there is a sufficient amount of the substantially monodispersed insulin polypeptide-oligomer conjugates to provide a concentration of the insulin peptide in portal vein blood between about 10 to 1,000 U/ml within about 60 minutes of administration.

3. The composition of claim 2 wherein the composition is fabricated for oral administration in a solid or liquid form.

4. The composition of claim 3 wherein conjugate of Formula V is in an amount sufficient to provide between about 0.05 to 10 mg per kilogram body weight of a subject receiving the composition.

5. The composition of claim 3 wherein the oral dose is in a solid form.

6. The composition of claim 1 wherein the insulin peptide drug is human insulin.

7. The composition of claim 1 wherein the conjugate of Formula V is amphiphilically balanced.

8. The composition of claim 1 wherein the composition is a pharmaceutical composition.

* * * * *